(12) United States Patent
Premack et al.

(10) Patent No.: US 8,088,895 B2
(45) Date of Patent: Jan. 3, 2012

(54) ANTIBODIES THAT BIND CXCR7 EPITOPES

(75) Inventors: Brett Premack, San Francisco, CA (US); Zhenhua Miao, San Jose, CA (US); Mark Penfold, Mountain View, CA (US)

(73) Assignee: ChemoCentryx, Inc., Mountain View, CA (US)

( * ) Notice: Subject to any disclaimer, the term of this patent is extended or adjusted under 35 U.S.C. 154(b) by 653 days.

(21) Appl. No.: 11/869,883

(22) Filed: Oct. 10, 2007

(65) Prior Publication Data

US 2009/0022717 A1 Jan. 22, 2009

Related U.S. Application Data

(60) Provisional application No. 60/852,745, filed on Oct. 18, 2006.

(51) Int. Cl.
*C07K 16/00* (2006.01)
(52) U.S. Cl. .................................. 530/387.1; 424/130.1
(58) Field of Classification Search .................... None
See application file for complete search history.

(56) References Cited

U.S. PATENT DOCUMENTS

| 7,678,891 B2 * | 3/2010 | Howard et al. | 530/388.22 |
| 2002/0166133 A1 * | 11/2002 | Barnes et al. | 800/8 |
| 2004/0170634 A1 | 9/2004 | Burns et al. | |
| 2005/0214287 A1 | 9/2005 | Burns et al. | |

FOREIGN PATENT DOCUMENTS

| WO | WO 2006/078780 A2 | 7/2006 |
| WO | WO 2006/116319 A2 | 11/2006 |

OTHER PUBLICATIONS

NCBI, Entrez Gene, http://www.ncbi.nlm.nih.gov/sites/entrez?Db=gene&Cmd=retrieve&dopt=full_report&list_uids=57007&log$=genesensor5&logdbfrom=pubmed. Retrieved on Mar. 25, 2010.*
Burns et al. (JEM, vol. 203, No. 9, p. 2201-2213, Sep. 4, 2006).*
Balabanian, K., et al.; "The Chemokine SDF-1/CXCL12 Binds to and Signals through the Orphan Receptor RDC1 in T Lymphocytes"; 2005, *The Journal of Biological Chemistry*, vol. 280, No. 42, pp. 35760-35766.
Infantino, S. et al.; "Expression and Regulation of the Orphan Receptor RDC1 and Its Putative Ligand in Human Dendritic and B Cells"; 2006, *The Journal of Immunology*, vol. 176, pp. 2197-2207.
Burns, Jennifer M. et al.; "A novel chemokine receptor for SDF-1 and I-TAC involved in cell survival, cell adhesion, and tumor development"; 2006, *The Journal of Experimental Medicine*, vol. 203, No. 9, pp. 2201-2213.
Genbank locus: AAH36661, 3 pages, Sep. 14, 2006.

* cited by examiner

*Primary Examiner* — Laura B Goddard
*Assistant Examiner* — Meera Natarajan
(74) *Attorney, Agent, or Firm* — Kilpatrick Townsend & Stockton LLP

(57) ABSTRACT

Antibodies that bind CXCR7 epitopes, as well as methods of identifying CXCR7 modulators are described.

12 Claims, 3 Drawing Sheets

Figure 1

For SEQ ID NO:23:
```
       <-------FR1---------->   <CDR1>   <-----FR2----->   <-------CDR2------>   <------------FR3------------>
    1  EVKLDETGGGLVQPGRPMKLSCVASGFTFS  DYWMN  WVRQSPEKGLEWVG  QIRNKPYNYETYSDSVKG  RFTISRDDSKSS VYLQMNLRTEDTGIYYCT-  99
```

For SEQ ID NO:25:
```
       <-------FR1---------->   <------CDR1------>   <-----FR2----->   <-CDR2-->   <------------FR3------------>
    1  DIVMTQSPSSLTVTAGEKVTMSC  KSSHSLLNSGIQKNFLT    WYQQKPGQPPKVLIY   WAFTRES     GVPERFTGSGSGTDFTLTISSVQAEDLAVYYC  QSDYTYP  101
```

For SEQ ID NO:27:
```
       <----------FR1---------->   <CDR1>   <-----FR2----->   <---CDR2-->   <------------FR3------------>
    1  EVKLVESGGDLVQPGGSLKLSCATSGFTFS  DYYMF  WVRQTPEKRLEWVA   YITNGGDRSYYSDTVTG  RFIISRDNAKNTLYLQMSRLKSEDTAMYYCAR  98
```

For SEQ ID NO:29:
```
       <-------FR1---------->   <-----CDR1----->   <-----FR2------>   <-CDR2--->   <------------FR3------------>
    1  DVLMTQTPLSLPVSLGDQASISC  RSSHYIVHSDGNTYLE    WYLQKPGQSPKLLIY   KVSNRFS     GVPDRFSGSGSGTDFTLKISRVEAEDLGIYYC  FQGSHVP  100
```

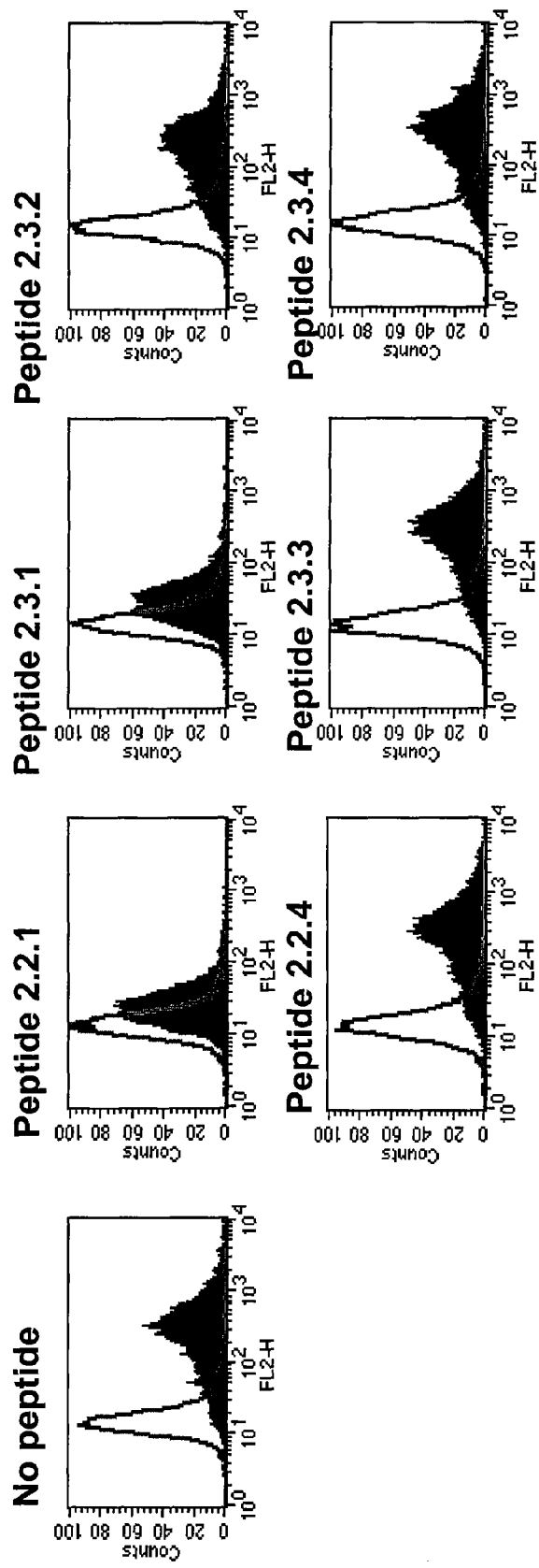
Figure 2: Peptide Inhibition on 11G8 Staining to 435-CXCR7 Cells

Figure 3: Ab Mapping Result Summary

| Peptide ID | Location | Peptide Sequence | 11G8 | 6E10 |
|---|---|---|---|---|
| Peptide 1 | N-terminus | M D L H L F D Y S E P G N F S D I | | |
| Peptide 2 | N-terminus | F S D I S W P C N S S D C I V V D | ■ | ■ |
| Peptide 3 | N-terminus | I V V D T V M C P N M P N K S V L L | | |
| Peptide 4 | 1 EC | Q H N Q W P M G E L T C | | |
| Peptide 5 | 2 EC | K T V T S A S N N E T Y C R S | | |
| Peptide 6 | 2 EC | Y C R S F Y P E H S I K E W L | | |
| Peptide 7 | 3 EC | S I L H Y I P F T C R L E H | | |
| Peptide 2 | N-terminus | F S D I S W P C N S S D C I V V D | | |
| Peptide 2.1.1 | N-terminus | D I S W P C N S S D C I | | |
| Peptide 2.1.2 | N-terminus | S W P C N S S D C I V V | | ■ |
| Peptide 2.1.3 | N-terminus | P C N S S D C I V V D T | | ■ |
| Peptide 2.1.4 | N-terminus | N S S D C I V V D T V M | | |
| Peptide 2.1.5 | N-terminus | S D C I V V D T V M C P | | |
| Peptide 2.1.6 | N-terminus | C I V V D T V M C P N M | | ■ |
| Peptide 2.1.7 | N-terminus | V V D T V M C P N M P N | | ■ |
| Peptide 9C4 | N-terminus | D Y S E P G N F S D I S W P C | | |
| Peptide 2 | N-terminus | F S D I S W P C N S S D C I V V D | ■ | |
| Peptide 2.2.1 | N-terminus | F S D I S W P C | ■ | |
| Peptide 2.2.2 | N-terminus | G N F S D I S W | | |
| Peptide 2.2.3 | N-terminus | M S D I N W P C (mCXCR7) | | |
| Peptide 2.2.4 | N-terminus | S W P C N S S D C I V | | |
| Peptide 2.2.5 | N-terminus | W P C N S S D C I V V | ■ | |
| Peptide 2.2.6 | N-terminus | N W P C N S S D C I V V (mCXCR7) | | |
| Peptide 2.2.1 | N-terminus | F S D I S W P C | | |
| Peptide 2.3.1 | N-terminus | N F S D I S W P | | |
| Peptide 2.3.2 | N-terminus | S D I N W P C N | | |
| Peptide 2.2.5 | N-terminus | W P C N S S D C I V V | | |
| Peptide 2.3.3 | N-terminus | W P C N S S D C I | | |
| Peptide 2.3.4 | N-terminus | P C N S S D C I V | | |

US 8,088,895 B2

SEQUENCE LISTING

<160> NUMBER OF SEQ ID NOS: 41

<210> SEQ ID NO 1
<211> LENGTH: 17
<212> TYPE: PRT
<213> ORGANISM: Artificial Sequence
<220> FEATURE:
<223> OTHER INFORMATION: CXCR7 Peptide #1

<400> SEQUENCE: 1

Met Asp Leu His Leu Phe Asp Tyr Ser Glu Pro Gly Asn Phe Ser Asp
 1               5                  10                  15

Ile

<210> SEQ ID NO 2
<211> LENGTH: 17
<212> TYPE: PRT
<213> ORGANISM: Artificial Sequence
<220> FEATURE:
<223> OTHER INFORMATION: CXCR7 Peptide #2

<400> SEQUENCE: 2

Phe Ser Asp Ile Ser Trp Pro Cys Asn Ser Ser Asp Cys Ile Val Val
 1               5                  10                  15

Asp

<210> SEQ ID NO 3
<211> LENGTH: 18
<212> TYPE: PRT
<213> ORGANISM: Artificial Sequence
<220> FEATURE:
<223> OTHER INFORMATION: CXCR7 Peptide #3

<400> SEQUENCE: 3

Ile Val Val Asp Thr Val Met Cys Pro Asn Met Pro Asn Lys Ser Val
 1               5                  10                  15

Leu Leu

<210> SEQ ID NO 4
<211> LENGTH: 12
<212> TYPE: PRT
<213> ORGANISM: Artificial Sequence
<220> FEATURE:
<223> OTHER INFORMATION: CXCR7 Peptide #4

<400> SEQUENCE: 4

Gln His Asn Gln Trp Pro Met Gly Glu Leu Thr Cys
 1               5                  10

<210> SEQ ID NO 5
<211> LENGTH: 15
<212> TYPE: PRT
<213> ORGANISM: Artificial Sequence
<220> FEATURE:
<223> OTHER INFORMATION: CXCR7 Peptide #5

<400> SEQUENCE: 5

Lys Thr Val Thr Ser Ala Ser Asn Asn Glu Thr Tyr Cys Arg Ser
 1               5                  10                  15

<210> SEQ ID NO 6
<211> LENGTH: 15
<212> TYPE: PRT
<213> ORGANISM: Artificial Sequence

```
<220> FEATURE:
<223> OTHER INFORMATION: CXCR7 Peptide #6

<400> SEQUENCE: 6

Tyr Cys Arg Ser Phe Tyr Pro Glu His Ser Ile Lys Glu Trp Leu
1               5                   10                  15

<210> SEQ ID NO 7
<211> LENGTH: 14
<212> TYPE: PRT
<213> ORGANISM: Artificial Sequence
<220> FEATURE:
<223> OTHER INFORMATION: CXCR7 Peptide #7

<400> SEQUENCE: 7

Ser Ile Leu His Tyr Ile Pro Phe Thr Cys Arg Leu Glu His
1               5                   10

<210> SEQ ID NO 8
<211> LENGTH: 12
<212> TYPE: PRT
<213> ORGANISM: Artificial Sequence
<220> FEATURE:
<223> OTHER INFORMATION: CXCR7 Peptide #2.1.1

<400> SEQUENCE: 8

Asp Ile Ser Trp Pro Cys Asn Ser Ser Asp Cys Ile
1               5                   10

<210> SEQ ID NO 9
<211> LENGTH: 12
<212> TYPE: PRT
<213> ORGANISM: Artificial Sequence
<220> FEATURE:
<223> OTHER INFORMATION: CXCR7 Peptide #2.1.2

<400> SEQUENCE: 9

Ser Trp Pro Cys Asn Ser Ser Asp Cys Ile Val Val
1               5                   10

<210> SEQ ID NO 10
<211> LENGTH: 12
<212> TYPE: PRT
<213> ORGANISM: Artificial Sequence
<220> FEATURE:
<223> OTHER INFORMATION: CXCR7 Peptide #2.1.3

<400> SEQUENCE: 10

Pro Cys Asn Ser Ser Asp Cys Ile Val Val Asp Thr
1               5                   10

<210> SEQ ID NO 11
<211> LENGTH: 15
<212> TYPE: PRT
<213> ORGANISM: Artificial Sequence
<220> FEATURE:
<223> OTHER INFORMATION: CXCR7 Peptide #9C4

<400> SEQUENCE: 11

Asp Tyr Ser Glu Pro Gly Asn Phe Ser Asp Ile Ser Trp Pro Cys
1               5                   10                  15

<210> SEQ ID NO 12
<211> LENGTH: 8
<212> TYPE: PRT
<213> ORGANISM: Artificial Sequence
<220> FEATURE:
<223> OTHER INFORMATION: CXCR7 Peptide #2.2.1
```

```
<400> SEQUENCE: 12

Phe Ser Asp Ile Ser Trp Pro Cys
1               5

<210> SEQ ID NO 13
<211> LENGTH: 8
<212> TYPE: PRT
<213> ORGANISM: Artificial Sequence
<220> FEATURE:
<223> OTHER INFORMATION: CXCR7 Peptide #2.2.2

<400> SEQUENCE: 13

Gly Asn Phe Ser Asp Ile Ser Trp
1               5

<210> SEQ ID NO 14
<211> LENGTH: 8
<212> TYPE: PRT
<213> ORGANISM: Artificial Sequence
<220> FEATURE:
<223> OTHER INFORMATION: mCXCR7 Peptide #2.2.3

<400> SEQUENCE: 14

Tyr Ser Asp Ile Asn Trp Pro Cys
1               5

<210> SEQ ID NO 15
<211> LENGTH: 11
<212> TYPE: PRT
<213> ORGANISM: Artificial Sequence
<220> FEATURE:
<223> OTHER INFORMATION: CXCR7 Peptide #2.2.4

<400> SEQUENCE: 15

Ser Trp Pro Cys Asn Ser Ser Asp Cys Ile Val
1               5                   10

<210> SEQ ID NO 16
<211> LENGTH: 11
<212> TYPE: PRT
<213> ORGANISM: Artificial Sequence
<220> FEATURE:
<223> OTHER INFORMATION: CXCR7 Peptide #2.2.5

<400> SEQUENCE: 16

Trp Pro Cys Asn Ser Ser Asp Cys Ile Val Val
1               5                   10

<210> SEQ ID NO 17
<211> LENGTH: 12
<212> TYPE: PRT
<213> ORGANISM: Artificial Sequence
<220> FEATURE:
<223> OTHER INFORMATION: mCXCR7 Peptide #2.2.6

<400> SEQUENCE: 17

Asn Trp Pro Cys Asn Ser Ser Asp Cys Ile Val Val
1               5                   10

<210> SEQ ID NO 18
<211> LENGTH: 8
<212> TYPE: PRT
<213> ORGANISM: Artificial Sequence
<220> FEATURE:
<223> OTHER INFORMATION: CXCR7 Peptide #2.3.1

<400> SEQUENCE: 18
```

```
Asn Phe Ser Asp Ile Ser Trp Pro
  1               5
```

<210> SEQ ID NO 19
<211> LENGTH: 8
<212> TYPE: PRT
<213> ORGANISM: Artificial Sequence
<220> FEATURE:
<223> OTHER INFORMATION: CXCR7 Peptide #2.3.2

<400> SEQUENCE: 19

```
Ser Asp Ile Asn Trp Pro Cys Asn
  1               5
```

<210> SEQ ID NO 20
<211> LENGTH: 9
<212> TYPE: PRT
<213> ORGANISM: Artificial Sequence
<220> FEATURE:
<223> OTHER INFORMATION: CXCR7 Peptide #2.3.3

<400> SEQUENCE: 20

```
Trp Pro Cys Asn Ser Ser Asp Cys Ile
  1               5
```

<210> SEQ ID NO 21
<211> LENGTH: 9
<212> TYPE: PRT
<213> ORGANISM: Artificial Sequence
<220> FEATURE:
<223> OTHER INFORMATION: CXCR7 Peptide #2.3.4

<400> SEQUENCE: 21

```
Pro Cys Asn Ser Ser Asp Cys Ile Val
  1               5
```

<210> SEQ ID NO 22
<211> LENGTH: 449
<212> TYPE: DNA
<213> ORGANISM: Artificial Sequence
<220> FEATURE:
<223> OTHER INFORMATION: anti-CXCR7 antibody 6E10 heavy chain variable
      region

<400> SEQUENCE: 22

```
atgtacttgg gactgagctg tgtattcatt gttttctct taaaaggtgt ccagtgtgag    60
gtgaagctgg atgagactgg aggaggcttg gtgcaacctg ggaggcccat gaaactctcc   120
tgtgttgcct ctggattcac ttttagtgac tactggatga actgggtccg ccagtctcca   180
gaaaaaggac tggagtgggt aggacaaatt agaaacaaac cttataatta tgaaacatat   240
tattcagatt ctgtgaaagg cagattcacc atctcaagag atgattccaa agtagtgtc    300 tacctgcaaa tgaacaactt aagaactgaa gacacgggta tctactactg tacatcctta   360
cgttactggg gccaaggaac tctggtcact gtctctgcag ccaaaacgac accccatcc   420 gtgtatcctg tggcccctgg aagcttggg                                      449
```

<210> SEQ ID NO 23
<211> LENGTH: 149
<212> TYPE: PRT
<213> ORGANISM: Artificial Sequence
<220> FEATURE:
<223> OTHER INFORMATION: anti-CXCR7 antibody 6E10 heavy chain variable
      region

<400> SEQUENCE: 23

```
Met Tyr Leu Gly Leu Ser Cys Val Phe Ile Val Phe Leu Leu Lys Gly
 1               5                  10                  15

Val Gln Cys Glu Val Lys Leu Asp Glu Thr Gly Gly Gly Leu Val Gln
            20                  25                  30

Pro Gly Arg Pro Met Lys Leu Ser Cys Val Ala Ser Gly Phe Thr Phe
        35                  40                  45

Ser Asp Tyr Trp Met Asn Trp Val Arg Gln Ser Pro Glu Lys Gly Leu
    50                  55                  60

Glu Trp Val Gly Gln Ile Arg Asn Lys Pro Tyr Asn Tyr Glu Thr Tyr
65                  70                  75                  80

Tyr Ser Asp Ser Val Lys Gly Arg Phe Thr Ile Ser Arg Asp Asp Ser
                85                  90                  95

Lys Ser Ser Val Tyr Leu Gln Met Asn Asn Leu Arg Thr Glu Asp Thr
            100                 105                 110

Gly Ile Tyr Tyr Cys Thr Ser Leu Arg Tyr Trp Gly Gln Gly Thr Leu
        115                 120                 125

Val Thr Val Ser Ala Ala Lys Thr Thr Pro Pro Ser Val Tyr Pro Val
    130                 135                 140

Ala Pro Gly Ser Leu
145

<210> SEQ ID NO 24
<211> LENGTH: 439
<212> TYPE: DNA
<213> ORGANISM: Artificial Sequence
<220> FEATURE:
<223> OTHER INFORMATION: anti-CXCR7 antibody 6E10 light chain variable
      region

<400> SEQUENCE: 24
atggtcctca tgtccttgct gttctgggta tctggtacct gtggggacat tgtgatgaca      60
cagtctccat cctccctgac tgtgacagca ggagagaagg tcactatgag ctgcaagtcc     120
agtcacagtc tgttaaacag tggaattcaa aagaacttct tgacctggta tcaacagaaa     180
ccagggcagc ctcctaaagt attgatctac tgggcattca ctaggaatc tggggtccct      240 gaacgcttca caggcagtgg atctggaaca gatttcactc tcaccatcag tagtgtgcag     300
gctgaagacc tggcagttta ttactgtcag agtgattata cttatccatt cacgttcggc     360
tcggggacaa agttggaaat aaaacgggct gatgctgcac caactgtatc catcttccca     420
ccatccagta agcttgggg                                                  439

<210> SEQ ID NO 25
<211> LENGTH: 146
<212> TYPE: PRT
<213> ORGANISM: Artificial Sequence
<220> FEATURE:
<223> OTHER INFORMATION: anti-CXCR7 antibody 6E10 light chain variable
      region

<400> SEQUENCE: 25

Met Val Leu Met Ser Leu Leu Phe Trp Val Ser Gly Thr Cys Gly Asp
 1               5                  10                  15

Ile Val Met Thr Gln Ser Pro Ser Ser Leu Thr Val Thr Ala Gly Glu
            20                  25                  30

Lys Val Thr Met Ser Cys Lys Ser Ser His Ser Leu Leu Asn Ser Gly
        35                  40                  45

Ile Gln Lys Asn Phe Leu Thr Trp Tyr Gln Gln Lys Pro Gly Gln Pro
    50                  55                  60
```

Pro Lys Val Leu Ile Tyr Trp Ala Phe Thr Arg Glu Ser Gly Val Pro
 65                  70                  75                  80

Glu Arg Phe Thr Gly Ser Gly Ser Gly Thr Asp Phe Thr Leu Thr Ile
             85                  90                  95

Ser Ser Val Gln Ala Glu Asp Leu Ala Val Tyr Tyr Cys Gln Ser Asp
            100                 105                 110

Tyr Thr Tyr Pro Phe Thr Phe Gly Ser Gly Thr Lys Leu Glu Ile Lys
        115                 120                 125

Arg Ala Asp Ala Ala Pro Thr Val Ser Ile Phe Pro Pro Ser Ser Lys
    130                 135                 140

Leu Gly
145

<210> SEQ ID NO 26
<211> LENGTH: 463
<212> TYPE: DNA
<213> ORGANISM: Artificial Sequence
<220> FEATURE:
<223> OTHER INFORMATION: anti-CXCR7 antibody 11G8 heavy chain variable
      region

<400> SEQUENCE: 26
atggagttgg ggttaaactg gttttccctt gtccttgttt taaaaggtgt ccagtgtgaa      60
gtgaagctgg tggagtctgg gggagacttg gtccagcctg agggtccct gaaactctcc     120 tgtgcaacct ctggattcac tttcagtgac tattacatgt tttgggttcg ccagactcca    180
gagaagaggc tggagtgggt cgcatacatt actaatgggg gtgatagaag ttattattca    240
gacactgtaa cgggccgatt catcatctcc agagacaatg ccaagaacac cctgtatctg    300
caaatgagcc gtctgaagtc tgaggacaca gccatgtatt actgtgcaag acaagggaac    360
tgggccgcct ggtttgttta ttggggccaa gggactctgg tcactgtttc tgcagccaaa    420
acgacacccc catccgttta tcccttggcc cctggaagct tgg                      463

<210> SEQ ID NO 27
<211> LENGTH: 154
<212> TYPE: PRT
<213> ORGANISM: Artificial Sequence
<220> FEATURE:
<223> OTHER INFORMATION: anti-CXCR7 antibody 11G8 heavy chain variable
      region

<400> SEQUENCE: 27

Met Glu Leu Gly Leu Asn Trp Val Phe Leu Val Leu Val Leu Lys Gly
  1               5                  10                  15

Val Gln Cys Glu Val Lys Leu Val Glu Ser Gly Gly Asp Leu Val Gln
             20                  25                  30

Pro Gly Gly Ser Leu Lys Leu Ser Cys Ala Thr Ser Gly Phe Thr Phe
         35                  40                  45

Ser Asp Tyr Tyr Met Phe Trp Val Arg Gln Thr Pro Glu Lys Arg Leu
     50                  55                  60

Glu Trp Val Ala Tyr Ile Thr Asn Gly Gly Asp Arg Ser Tyr Tyr Ser
 65                  70                  75                  80

Asp Thr Val Thr Gly Arg Phe Ile Ile Ser Arg Asp Asn Ala Lys Asn
             85                  90                  95

Thr Leu Tyr Leu Gln Met Ser Arg Leu Lys Ser Glu Asp Thr Ala Met
            100                 105                 110

Tyr Tyr Cys Ala Arg Gln Gly Asn Trp Ala Ala Trp Phe Val Tyr Trp
        115                 120                 125

Gly Gln Gly Thr Leu Val Thr Val Ser Ala Ala Lys Thr Thr Pro Pro
            130                 135                 140

Ser Val Tyr Pro Leu Ala Pro Gly Ser Leu
145                 150

<210> SEQ ID NO 28
<211> LENGTH: 447
<212> TYPE: DNA
<213> ORGANISM: Artificial Sequence
<220> FEATURE:
<223> OTHER INFORMATION: anti-CXCR7 antibody 11G8 light chain variable
      region

<400> SEQUENCE: 28
atgaagttgc ctgttaggct gttggtgctg atgttctgga ttcctgcttc caccagtgat      60
gttttgatga cccaaactcc actctccctg cctgtcagtc ttggagatca agcctccatc     120
tcttgcagat ctagtcacta tattgtacat agtgacggaa acacctattt agagtggtac     180
ctgcagaaac aggccagtc tccaaagctc ctgatctaca agtttccaa ccgattttct     240 ggggtcccag acaggttcag tggcagtgga tcagggacag atttcacact caagatcagc     300
agagtggagg ctgaggatct gggaatttat tactgctttc aaggttcaca tgttccgctc     360
acgttcggtg ctgggaccaa gctggagctg aaacgggctg atgctgcacc aactgtatcc     420
atcttcccac catccagtaa gcttggg                                        447

<210> SEQ ID NO 29
<211> LENGTH: 149
<212> TYPE: PRT
<213> ORGANISM: Artificial Sequence
<220> FEATURE:
<223> OTHER INFORMATION: anti-CXCR7 antibody 11G8 light chain variable
      region

<400> SEQUENCE: 29

Met Lys Leu Pro Val Arg Leu Leu Val Leu Met Phe Trp Ile Pro Ala
1               5                   10                  15

Ser Thr Ser Asp Val Leu Met Thr Gln Thr Pro Leu Ser Leu Pro Val
            20                  25                  30

Ser Leu Gly Asp Gln Ala Ser Ile Ser Cys Arg Ser His Tyr Ile
        35                  40                  45

Val His Ser Asp Gly Asn Thr Tyr Leu Glu Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Ile Tyr Tyr Cys
            100                 105                 110

Phe Gln Gly Ser His Val Pro Leu Thr Phe Gly Ala Gly Thr Lys Leu
        115                 120                 125

Glu Leu Lys Arg Ala Asp Ala Ala Pro Thr Val Ser Ile Phe Pro Pro
    130                 135                 140

Ser Ser Lys Leu Gly
145

<210> SEQ ID NO 30
<211> LENGTH: 362
<212> TYPE: PRT
<213> ORGANISM: Homo sapiens
<220> FEATURE:
<223> OTHER INFORMATION: presumed G-protein coupled receptor (GPCR) CXCR7, RDC1, CCX-CKR2

<400> SEQUENCE: 30

```
Met Asp Leu His Leu Phe Asp Tyr Ser Glu Pro Gly Asn Phe Ser Asp
  1               5                  10                  15

Ile Ser Trp Pro Cys Asn Ser Ser Asp Cys Ile Val Val Asp Thr Val
             20                  25                  30

Met Cys Pro Asn Met Pro Asn Lys Ser Val Leu Leu Tyr Thr Leu Ser
         35                  40                  45

Phe Ile Tyr Ile Phe Ile Phe Val Ile Gly Met Ile Ala Asn Ser Val
 50                  55                  60

Val Val Trp Val Asn Ile Gln Ala Lys Thr Thr Gly Tyr Asp Thr His
 65                  70                  75                  80

Cys Tyr Ile Leu Asn Leu Ala Ile Ala Asp Leu Trp Val Val Leu Thr
                 85                  90                  95

Ile Pro Val Trp Val Val Ser Leu Val Gln His Asn Gln Trp Pro Met
            100                 105                 110

Gly Glu Leu Thr Cys Lys Val Thr His Leu Ile Phe Ser Ile Asn Leu
        115                 120                 125

Phe Gly Ser Ile Phe Phe Leu Thr Cys Met Ser Val Asp Arg Tyr Leu
130                 135                 140

Ser Ile Thr Tyr Phe Thr Asn Thr Pro Ser Ser Arg Lys Lys Met Val
145                 150                 155                 160

Arg Arg Val Val Cys Ile Leu Val Trp Leu Leu Ala Phe Cys Val Ser
                165                 170                 175

Leu Pro Asp Thr Tyr Tyr Leu Lys Thr Val Thr Ser Ala Ser Asn Asn
            180                 185                 190

Glu Thr Tyr Cys Arg Ser Phe Tyr Pro Glu His Ser Ile Lys Glu Trp
        195                 200                 205

Leu Ile Gly Met Glu Leu Val Ser Val Val Leu Gly Phe Ala Val Pro
210                 215                 220

Phe Ser Ile Ile Ala Val Phe Tyr Phe Leu Leu Ala Arg Ala Ile Ser
225                 230                 235                 240

Ala Ser Ser Asp Gln Glu Lys His Ser Ser Arg Lys Ile Ile Phe Ser
                245                 250                 255

Tyr Val Val Val Phe Leu Val Cys Trp Leu Pro Tyr His Val Ala Val
            260                 265                 270

Leu Leu Asp Ile Phe Ser Ile Leu His Tyr Ile Pro Phe Thr Cys Arg
        275                 280                 285

Leu Glu His Ala Leu Phe Thr Ala Leu His Val Thr Gln Cys Leu Ser
290                 295                 300

Leu Val His Cys Cys Val Asn Pro Val Leu Tyr Ser Phe Ile Asn Arg
305                 310                 315                 320

Asn Tyr Arg Tyr Glu Leu Met Lys Ala Phe Ile Phe Lys Tyr Ser Ala
                325                 330                 335

Lys Thr Gly Leu Thr Lys Leu Ile Asp Ala Ser Arg Val Ser Glu Thr
            340                 345                 350

Glu Tyr Ser Ala Leu Glu Gln Ser Thr Lys
        355                 360

<210> SEQ ID NO 31
<211> LENGTH: 99
<212> TYPE: PRT
<213> ORGANISM: Artificial Sequence
```

-continued

<220> FEATURE:
<223> OTHER INFORMATION: anti-CXCR7 antibody gE10 heavy chain variable
      region FR1, CDR1, FR2, CDR2 and FR3

<400> SEQUENCE: 31

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Gly Gln Ile Arg Asn Lys Pro Tyr Asn Tyr Glu Thr Tyr Tyr Ser Asp
50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Thr Glu Asp Thr Gly Ile Tyr
                85                  90                  95

Tyr Cys Thr

<210> SEQ ID NO 32
<211> LENGTH: 101
<212> TYPE: PRT
<213> ORGANISM: Artificial Sequence
<220> FEATURE:
<223> OTHER INFORMATION: anti-CXCR7 antibody 6E10 light chain variable
      region FR1, CDR1, FR2, CDR2 and FR3

<400> SEQUENCE: 32

Asp Ile Val Met Thr Gln Ser Pro Ser Ser Leu Thr Val Thr Ala Gly
1               5                   10                  15

Glu Lys Val Thr Met Ser Cys Lys Ser Ser His Ser Leu Leu Asn Ser
            20                  25                  30

Gly Ile Gln Lys Asn Phe Leu Thr Trp Tyr Gln Gln Lys Pro Gly Gln
        35                  40                  45

Pro Pro Lys Val Leu Ile Tyr Trp Ala Phe Thr Arg Glu Ser Gly Val
50                  55                  60

Pro Glu Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Ser
                85                  90                  95

Asp Tyr Thr Tyr Pro
                100

<210> SEQ ID NO 33
<211> LENGTH: 98
<212> TYPE: PRT
<213> ORGANISM: Artificial Sequence
<220> FEATURE:
<223> OTHER INFORMATION: anti-CXCR7 antibody 11G8 heavy chain variable
      region FR1, CDR1, FR2, CDR2 and FR3

<400> SEQUENCE: 33

Glu Val Lys Leu Val Glu Ser Gly Gly Asp Leu Val Gln Pro Gly Gly
1               5                   10                  15

Ser Leu Lys Leu Ser Cys Ala Thr Ser Gly Phe Thr Phe Ser Asp Tyr
            20                  25                  30

Tyr Met Phe Trp Val Arg Gln Thr Pro Glu Lys Arg Leu Glu Trp Val
        35                  40                  45

Ala Tyr Ile Thr Asn Gly Gly Asp Arg Ser Tyr Tyr Ser Asp Thr Val
50                  55                  60

```
Thr Gly Arg Phe Ile Ile Ser Arg Asp Asn Ala Lys Asn Thr Leu Tyr
 65                  70                  75                  80

Leu Gln Met Ser Arg Leu Lys Ser Glu Asp Thr Ala Met Tyr Tyr Cys
                 85                  90                  95

Ala Arg

<210> SEQ ID NO 34
<211> LENGTH: 100
<212> TYPE: PRT
<213> ORGANISM: Artificial Sequence
<220> FEATURE:
<223> OTHER INFORMATION: anti-CXCR7 antibody 11G8 light chain variable
      region FR1, CDR1, FR2, CDR2 and FR3

<400> SEQUENCE: 34

Asp Val Leu Met Thr Gln Thr Pro Leu Ser Leu Pro Val Ser Leu Gly
  1               5                  10                  15

Asp Gln Ala Ser Ile Ser Cys Arg Ser Ser His Tyr Ile Val His Ser
                 20                  25                  30

Asp Gly Asn Thr Tyr Leu Glu Trp Tyr Leu Gln Lys Pro Gly Gln Ser
             35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Ile Tyr Tyr Cys Phe Gln Gly
                 85                  90                  95

Ser His Val Pro
            100

<210> SEQ ID NO 35
<211> LENGTH: 12
<212> TYPE: PRT
<213> ORGANISM: Artificial Sequence
<220> FEATURE:
<223> OTHER INFORMATION: CXCR7 Peptide #2.1.4

<400> SEQUENCE: 35

Asn Ser Ser Asp Cys Ile Val Val Asp Thr Val Met
  1               5                  10

<210> SEQ ID NO 36
<211> LENGTH: 12
<212> TYPE: PRT
<213> ORGANISM: Artificial Sequence
<220> FEATURE:
<223> OTHER INFORMATION: CXCR7 Peptide #2.1.5

<400> SEQUENCE: 36

Ser Asp Cys Ile Val Val Asp Thr Val Met Cys Pro
  1               5                  10

<210> SEQ ID NO 37
<211> LENGTH: 12
<212> TYPE: PRT
<213> ORGANISM: Artificial Sequence
<220> FEATURE:
<223> OTHER INFORMATION: CXCR7 Peptide #2.1.6

<400> SEQUENCE: 37

Cys Ile Val Val Asp Thr Val Met Cys Pro Asn Met
  1               5                  10
```

```
<210> SEQ ID NO 38
<211> LENGTH: 12
<212> TYPE: PRT
<213> ORGANISM: Artificial Sequence
<220> FEATURE:
<223> OTHER INFORMATION: CXCR7 Peptide #2.1.7

<400> SEQUENCE: 38

Val Val Asp Thr Val Met Cys Pro Asn Met Pro Asn
1               5                   10

<210> SEQ ID NO 39
<211> LENGTH: 7
<212> TYPE: PRT
<213> ORGANISM: Artificial Sequence
<220> FEATURE:
<223> OTHER INFORMATION: anti-CXCR7 antibody 11G8 minimal epitope

<400> SEQUENCE: 39

Phe Ser Asp Ile Ser Trp Pro
1               5

<210> SEQ ID NO 40
<211> LENGTH: 10
<212> TYPE: PRT
<213> ORGANISM: Artificial Sequence
<220> FEATURE:
<223> OTHER INFORMATION: anti-CXCR7 antibody 6E10 minimal epitope

<400> SEQUENCE: 40

Trp Pro Cys Asn Ser Ser Asp Cys Ile Val
1               5                   10

<210> SEQ ID NO 41
<211> LENGTH: 5
<212> TYPE: PRT
<213> ORGANISM: Artificial Sequence
<220> FEATURE:
<223> OTHER INFORMATION: single chain Fv (scFv) antibody peptide linker

<400> SEQUENCE: 41

Gly Gly Gly Gly Ser
1               5
```

ANTIBODIES THAT BIND CXCR7 EPITOPES

CROSS-REFERENCE TO RELATED PATENT APPLICATIONS

The present application claims benefit of priority to U.S. Provisional Patent Application No. 60/852,745, filed Oct. 18, 2006, which is incorporated by reference.

BACKGROUND OF THE INVENTION

Chemokines constitute a family of small cytokines that are, inter alia, produced in inflammation and regulate leukocyte recruitment, activation and proliferation (Baggiolini, M. et al., *Adv. Immunol.* 55: 97-179 (1994); Springer, T. A., *Annu. Rev. Physiol* 57: 827-872 (1995); and Schall, T. J. and K. B. Bacon, *Curr. Opin. Immunol.* 6: 865-873 (1994)). Chemokines are capable of selectively inducing chemotaxis of the formed elements of the blood (other than red blood cells), including leukocytes such as neutrophils, monocytes, macrophages, eosinophils, basophils, mast cells, and lymphocytes, including T cells and B cells. In addition to stimulating chemotaxis, other changes can be selectively induced by chemokines in responsive cells, including changes in cell shape, transient rises in the concentration of intracellular free calcium ions ($Ca^{2+}$), granule exocytosis, integrin upregulation, formation of bioactive lipids (e.g., leukotrienes), expression of cytokines, and respiratory burst, associated with leukocyte activation, growth and proliferation. Thus, the chemokines are early triggers of the inflammatory response, causing inflammatory mediator release, chemotaxis and extravasation to sites of infection or inflammation.

Two subfamilies of chemokines, designated as CXC and CC chemokines, are distinguished by the arrangement of the first two of four conserved cysteine residues, which are either separated by one amino acid (as in CXC chemokines SDF-1, IL-8, IP-10, MIG, PF4, ENA-78, GCP-2, GROα, GROβ, GROγ, NAP-2, NAP-4, I-TAC) or are adjacent residues (as in CC chemokines MIP-1α, MIP-1β, RANTES, MCP-1, MCP-2, MCP-3, I-309). Most CXC chemokines attract neutrophil leukocytes. For example, the CXC chemokines interleukin 8 (IL-8), platelet factor 4 (PF4), and neutrophil-activating peptide 2 (NAP-2) are potent chemoattractants and activators of neutrophils. The CXC chemokines designated MIG (monokine induced by gamma interferon) and IP-10 (interferon-γ inducible 10 kDa protein) are particularly active in inducing chemotaxis of activated peripheral blood lymphocytes. CC chemokines are generally less selective and can attract a variety of leukocyte cell types, including monocytes, eosinophils, basophils, T lymphocytes, granulocytes and natural killer cells. CC chemokines such as human monocyte chemotactic proteins 1-3 (MCP-1, MCP-2 and MCP-3), RANTES (Regulated on Activation, Normal T Expressed and Secreted), and the macrophage inflammatory proteins 1α and 1β (MIP-1α and MIP-1β) have been characterized as chemoattractants and activators of monocytes or lymphocytes, but do not appear to be chemoattractants for neutrophils.

CC and CXC chemokines act through receptors that belong to a superfamily of seven transmembrane spanning G protein-coupled receptors (Murphy, P. M., *Pharmacol Rev.* 52:145-176 (2000)). This family of G-protein coupled receptors comprises a large group of integral membrane proteins, containing seven transmembrane-spanning regions. The receptors may be coupled to G proteins, which are heterotrimeric regulatory proteins capable of binding GTP and mediating signal transduction from coupled receptors, for example, by the production of intracellular mediators. Additionally chemokine receptors may act independently of G protein coupling. For instance the Duffy receptor expressed predominantly on red blood cells is a promiscuous chemokine binding receptor which is believed to act as a chemokine, removing chemokines from the circulatory environment.

Generally speaking, chemokine and chemokine receptor interactions tend to be promiscuous in that one chemokine can bind many chemokine receptors and conversely a single chemokine receptor can interact with several chemokines There are many aspects of chemokine receptor signaling and selectivity for ligands that were not previously understood. For example, there are a number of orphan receptors for which no function has been previously determined. RDC1, for example, though earlier thought to be a receptor for vasoactive intestinal peptide (VIP), until recently has been considered to be an orphan receptor because its endogenous ligand has not been identified. See, e.g., Cook et al., *FEBS Letts.* 300(2): 149-152 (1992).

Recently, RDC1, renamed as CXCR7, was determined to bind to both chemokines SDF-1 and I-TAC. See, e.g., PCT/US04/34807 and U.S. patent application Ser. Nos. 10/698,541, 10/912,638 and 11/050,345, each of which are incorporated by reference in their entirety.

BRIEF SUMMARY OF THE INVENTION

The present invention provides antibodies that bind to epitopes of CXCR7. In some embodiments, the invention provides an antibody that binds to:

a polypeptide consisting of FSDISWPC (SEQ ID NO:12); or a polypeptide consisting of SWPCNSSDCIVV (SEQ ID NO:15); or other CXCR7 epitopes as described herein.

In some embodiments, the antibody is linked to a detectable label. In some embodiments, the antibody is a monoclonal antibody. In some embodiments, the antibody is a humanized antibody. In some embodiments, the antibody binds to the polypeptide consisting of FSDISWPC (SEQ ID NO:12). In some embodiments, the antibody binds to the polypeptide consisting of SWPCNSSDCIVV (SEQ ID NO:15). In some embodiments, the antibody competes with SDF-1 for binding to CXCR7.

The present invention also provides pharmaceutical compositions comprising a pharmaceutically acceptable excipient and an antibody that binds to:

a polypeptide consisting of FSDISWPC (SEQ ID NO:12); or a polypeptide consisting of SWPCNSSDCIVV (SEQ ID NO:15); or other CXCR7 epitopes as described herein.

In some embodiments, the antibody is a monoclonal antibody. In some embodiments, the antibody is a humanized antibody. In some embodiments, the antibody binds to the polypeptide consisting of FSDISWPC (SEQ ID NO:12). In some embodiments, the antibody binds to the polypeptide consisting of SWPCNSSDCIVV (SEQ ID NO:15).

The present invention also provides methods of detecting a cell expressing CXCR7 in a biological sample. In some embodiments, the methods comprise contacting the biological sample with an antibody and detecting the presence of the antibody, wherein the antibody binds to:

a polypeptide consisting of FSDISWPC (SEQ ID NO:12); or a polypeptide consisting of SWPCNSSDCIVV (SEQ ID NO:15); or other CXCR7 epitopes as described herein.

The present invention also provides for treating, preventing or ameliorating a disease, the method comprising administering an antibody to an individual in need thereof, wherein the antibody binds to:

a polypeptide consisting of FSDISWPC (SEQ ID NO:12); or a polypeptide consisting of SWPCNSSDCIVV (SEQ ID NO:15); or other CXCR7 epitopes as described herein.

The present invention also provides methods of inhibiting proliferation of a cancer cell. In some embodiments, the methods comprise administering an antibody to an individual in need thereof, wherein the antibody binds to:

a polypeptide consisting of FSDISWPC (SEQ ID NO:12); or a polypeptide consisting of SWPCNSSDCIVV (SEQ ID NO:15); or other CXCR7 epitopes as described herein.

The present invention also provides methods of inhibiting angiogenesis or vascularization. In some embodiments, the methods comprise administering an antibody to an individual in need thereof, wherein the antibody binds to:

a polypeptide consisting of FSDISWPC (SEQ ID NO:12); or a polypeptide consisting of SWPCNSSDCIVV (SEQ ID NO:15); or other CXCR7 epitopes as described herein.

In some embodiments, the individual has or is pre-disposed to have arthritis. In some embodiments, the individual has cancer.

The present invention also provides methods for identifying a modulator of CXCR7. In some embodiments, the methods comprise:

(a) contacting a test agent to a polypeptide comprising a fragment of CXCR7 (e.g., having no more than 250 contiguous amino acids of SEQ ID NO:30) and wherein the polypeptide comprises minimum epitopes FSDISWP (SEQ ID NO:39) or WPCNSSDCIV (SEQ ID NO:40) or polypeptides FSDISWPC (SEQ ID NO:12) or SWPCNSSDCIVV (SEQ ID NO:15); and (b) selecting an agent that binds to the polypeptide, wherein binding of the test agent to the polypeptide is an indication that the test agent is a modulator of CXCR7 activity.

In some embodiments, the selecting step comprises measuring the ability of the test agent to compete with SDF-1 or I-TAC for binding to the polypeptide. In some embodiments, the polypeptide has no more than 50 contiguous amino acids of SEQ ID NO:30.

In some embodiments, the antibodies of the present invention bind to polypeptides consisting of any of SEQ ID NOS:2, 8, 9, 11, 12, 14, 15, 16, 17, or as otherwise disclosed herein.

In some embodiments, the antibodies of the present invention do not include anti-RDC1 antibodies (such as antibody "9C4") disclosed in Balbanian et al., *J. Biologic. Chem.* 280 (42):35760-35766 (2005). In some embodiments, the antibodies that bind to the epitopes described herein do not include antibodies 11G8 or 6E10 and/or do not comprise the variable regions displayed in FIG. 1 or other anti-CXCR7 antibodies described in PCT/US06/15492. In some embodiments, the antibody does not comprise the complementarity determining regions (CDRs) of the variable regions displayed in SEQ ID NO:23, SEQ ID NO:25, SEQ ID NO:27, or SEQ ID NO:29.

BRIEF DESCRIPTION OF THE DRAWINGS

FIG. 1 depicts some embodiments of some of the complementarity determining regions (CDRs) of the antibodies of the invention (SEQ ID NOS: 31-34 from SEQ ID NOS:23, 25, 27, and 29, respectively).

FIG. 2 illustrates results of peptide inhibition on 11G8 staining to 435-CXCR7 cells.

FIG. 3 illustrates a summary of peptide competition experiments for antibodies 11G8 and 6E10 (SEQ ID NOS:1-7, 2, 8-10, 35-38, 11, 2, 12-17, 12, 18, 19, 16, 20 and 21, respectively).

DEFINITIONS

"RDC1" designated herein as "CXCR7" (also known as "CCX-CKR2"), refers to a seven-transmembrane domain presumed G-protein coupled receptor (GPCR). See, e.g., Burns et al, *J Exp Med.* 203(9):2201-13 (2006). The CXCR7 dog ortholog was originally identified in 1991. See, Libert et al. *Science* 244:569-572 (1989). The dog sequence is described in Libert et al., *Nuc. Acids Res.* 18(7):1917 (1990). The mouse sequence is described in, e.g., Heesen et al, *Immunogenetics* 47:364-370 (1998). The human sequence is described in, e.g., Sreedharan et al., *Proc. Natl. Acad. Sci. USA* 88:4986-4990 (1991), which mistakenly described the protein as a receptor of vasoactive intestinal peptide. "CXCR7" includes SEQ ID NO:30 as well as sequences that are conservatively modified variants of SEQ ID NO:30. See, e.g., PCT/US04/34807. Fragments of CXCR7 are fragments of at least 5, and sometimes at least 10, 20, 50, 100, 200, 300 or up to 300 contiguous amino acids of one of the above-listed sequences, or a conservatively modified variant thereof.

An antibody that "binds" to a particular polypeptide refers to an antibody that competes with the polypeptide for binding to CXCR7 (e.g., SEQ ID NO:30) as expressed on a cell and as measured by FACS.

A "subject" or "individual" refers to an animal, including a human, non-human primate, mouse, rat, dog or other mammal.

A "chemotherapeutic agent" refers to an agent, which when administered to an individual is sufficient to cause inhibition, slowing or arresting of the growth of cancerous cells, or is sufficient to produce a cytotoxic effect in cancerous cells.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

Naturally occurring immunoglobulins have a common core structure in which two identical light chains (about 24 kD) and two identical heavy chains (about 55 or 70 kD) form a tetramer. The amino-terminal portion of each chain is known as the variable (V) region and can be distinguished from the more conserved constant (C) regions of the remainder of each chain. Within the variable region of the light chain is a C-terminal portion known as the J region. Within the variable region of the heavy chain, there is a D region in addition to the J region. Most of the amino acid sequence variation in immunoglobulins is confined to three separate locations in the V regions known as hypervariable regions or complementarity determining regions (CDRs) which are directly involved in antigen binding. Proceeding from the amino-terminus, these regions are designated CDR1, CDR2 and CDR3, respectively. The CDRs are held in place by more conserved framework regions (FRs). Proceeding from the amino-terminus, these regions are designated FR1, FR2, FR3, and FR4, respectively. The locations of CDR and FR regions and a numbering system have been defined by, e.g., Kabat et al. (Kabat et al., Sequences of Proteins of Immunological Interest, Fifth Edition, U.S. Department of Health and Human Services, U.S. Government Printing Office (1991)).

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_{H1}$ by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see FUNDAMENTAL IMMUNOLOGY (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)).

For preparation of monoclonal or polyclonal antibodies, any technique known in the art can be used (see, e.g., Kohler & Milstein, Nature 256:495-497 (1975); Kozbor et al., Immunology Today 4:72 (1983); Cole et al., pp. 77-96 in Monoclonal Antibodies and Cancer Therapy (1985)). "Monoclonal" antibodies refer to antibodies derived from a single clone. Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., Nature 348:552-554 (1990); Marks et al., Biotechnology 10:779-783 (1992)).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

A "humanized" antibody is an antibody that retains the reactivity of a non-human antibody while being less immunogenic in humans. This can be achieved, for instance, by retaining the non-human CDR regions and replacing the remaining parts of the antibody with their human counterparts. See, e.g., Morrison et al., Proc. Natl. Acad. Sci. USA, 81:6851-6855 (1984); Morrison and Oi, Adv. Immunol., 44:65-92 (1988); Verhoeyen et al., Science, 239:1534-1536 (1988); Padlan, Molec. Immun., 28:489-498 (1991); Padlan, Molec. Immun., 31(3):169-217 (1994).

The term "isolated," when applied to a protein, denotes that the protein is essentially free of other cellular components with which it is associated in the natural state. It is preferably in a homogeneous state although some trace impurities may exist. It can be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. The term "purified" denotes that a protein gives rise to essentially one band in an electrophoretic gel. Particularly, it means that the protein is at least 85% pure, more preferably at least 95% pure, and most preferably at least 99% pure.

The phrase "specifically (or selectively) binds" to an antibody or "specifically (or selectively) immunoreactive with," when referring to a protein, glycoprotein or peptide, refers to a binding reaction that is determinative of the presence of the protein in a heterogeneous population of proteins and other biologics (such as a cell lysate). Thus, under designated immunoassay conditions, the specified antibodies bind to a particular protein at least two times the background and do not substantially bind in a significant amount to other proteins present in the sample. Typically a specific or selective reaction will be at least twice background signal or noise and more typically more than 10 to 100 times background.

The terms "peptidomimetic" and "mimetic" refer to a synthetic chemical compound that has substantially the same structural and functional characteristics of a naturally or non-naturally occurring polypeptide (e.g., a reagent that binds to CXCR7). Peptide analogs are commonly used in the pharmaceutical industry as non-peptide drugs with properties analogous to those of the template peptide. These types of non-peptide compound are termed "peptide mimetics" or "peptidomimetics" (Fauchere, J. Adv. Drug Res. 15:29 (1986); Veber and Freidinger TINS p. 392 (1985); and Evans et al. J. Med. Chem. 30:1229 (1987), which are incorporated herein by reference). Peptide mimetics that are structurally similar to therapeutically useful peptides may be used to produce an equivalent or enhanced therapeutic or prophylactic effect. Generally, peptidomimetics are structurally similar to a paradigm polypeptide (i.e., a polypeptide that has a biological or pharmacological activity), such as found in a polypeptide of interest, but have one or more peptide linkages optionally replaced by a linkage selected from the group consisting of, e.g., —$CH_2NH$—, —$CH_2S$—, —$CH_2$—$CH_2$—, —$CH$=$CH$— (cis and trans), —$COCH_2$—, —$CH(OH)CH_2$—, and —$CH_2SO$—. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity. For example, a mimetic composition is within the scope of the invention if it is capable of carrying out at least one of the binding or enzymatic activities of a polypeptide of interest.

A "ligand" refers to an agent, e.g., a polypeptide or other molecule, capable of binding to a receptor.

"Conservatively modified variants" applies to both amino acid and nucleic acid sequences. With respect to particular nucleic acid sequences, "conservatively modified variants" refers to those nucleic acids that encode identical or essentially identical amino acid sequences, or where the nucleic acid does not encode an amino acid sequence, to essentially identical sequences. Because of the degeneracy of the genetic code, a number of nucleic acid sequences will encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, Proteins (1984)).

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, or 95% identity over a specified region, e.g., of the entire polypeptide sequences of the invention or the extra-cellular domains of the polypeptides of the invention), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. Optionally, the identity exists over a region that is at least about 50 nucleotides in length, or more preferably over a region that is 100 to 500 or 1000 or more nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of, e.g., a full length sequence or from 20 to 600, about 50 to about 200, or about 100 to about 150 amino acids or nucleotides in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

An example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

DETAILED DESCRIPTION OF THE INVENTION

I. Introduction

The present invention provides for the identification of epitopes of antibodies that compete for binding of the SDF-1 and I-TAC chemokines to CXCR7. Thus, the present invention provides antibodies that bind epitopes of CXCR7 that are involved in ligand binding and/or signaling. In addition, methods of screening for agents that bind to the epitopes are also provided as those methods are useful for identifying antagonist and agonist agents useful in modulating signaling through the CXCR7 receptor.

The antibodies designated 11G8 and 6E10 compete with SDF-1 for binding on CXCR7 and therefore the epitopes bound by the antibodies were mapped. The peptides displayed in Table 1 were tested for their ability to compete with the antibodies for binding.

TABLE 1

| SEQ ID NO: | Peptide # | Peptide |
|---|---|---|
| 1 | 1 | MDLHLFDYSEPGNFSDI |
| 2 | 2 | FSDISWPCNSSDCIVVD |
| 3 | 3 | IVVDTVMCPNMPNKSVLL |
| 4 | 4 | QHNQWPMGELTC |
| 5 | 5 | KTVTSASNNETYCRS |
| 6 | 6 | YCRSFYPEHSIKEWL |
| 7 | 7 | SILHYIPFTCRLEH |
| 8 | 2.1.1 | DISWPCNSSDCI |
| 9 | 2.1.2 | SWPCNSSDCIVV |
| 10 | 2.1.3 | PCNSSDCIVVDT |
| 11 | 9C4 | DYSEPGNFSDISWPC |
| 12 | 2.2.1. | FSDISWPC |
| 13 | 2.2.2 | GNFSDISW |
| 14 | 2.2.3 | YSDINWPC |
| 15 | 2.2.4 | SWPCNSSDCIV |
| 16 | 2.2.5 | WPCNSSDCIVV |
| 17 | 2.2.6 | NWPCNSSDCIVV |
| 18 | 2.3.1 | NFSDISWP |
| 19 | 2.3.2 | SDINWPCN |
| 20 | 2.3.3 | WPCNSSDCI |
| 21 | 2.3.4 | PCNSSDCIV |

SEQ ID NOS: 2, 11, 12, 14, and 18 competed with antibody 11G8.
SEQ ID NOS: 2, 8, 9, 15, 16, and 17 competed with antibody 6E10.
The minimal epitope of antibody 11G8 was determined to be FSDISWP (SEQ ID NO: 39) and the minimal epitope of antibody 6E10 was determined to be WPCNSSDCIV (SEQ ID NO: 40).

II. Antibodies of the Invention

The present invention provides antibodies that bind to any of SEQ ID NOS:2, 8, 9, 11, 12, 14, 15, 16, 17 or other epitopes as described herein. The present invention provides reagents and methods for treatment, diagnosis and prognosis for diseases and disorders related to CXCR7 using antibodies against CXCR7. Diseases and disorders related to CXCR7 are exemplified more below and include, but are not limited to, cancer, diseases involving excessive or abnormal angiogenesis and arthritis.

In some embodiments, the antibodies are isolated. In some embodiments the antibodies bind to CXCR7 and compete with the chemokines SDF-1 and I-TAC for binding to CXCR7. Competition assays for CXCR7 binding are described in, e.g., PCT/US04/34807 and U.S. Patent Publication Nos. US2004/0170634 and 2005/0074826. Competition of antibody binding is determined by a reduction of antibody binding in the presence of peptide when compared with antibody alone. Competition is indicated by a shift of 0.5 logs, preferably 1 logs, more preferably 2 logs or higher as measured by FACS.

In some embodiments of the invention, the antibodies bind to CXCR7 but do not bind to human peripheral blood. For example, in some embodiments, the antibodies of the invention do not bind to at least one of the following: basophils, monocytes, plasmacytoid dendritic cells; B cells, or CD4$^+$ T cells.

The locations of CDR and FR regions and a numbering system have been described previously, e.g., Kabat et al. (Kabat et al., Sequences of Proteins of Immunological Interest, Fifth Edition, U.S. Department of Health and Human Services, U.S. Government Printing Office (1991)). CDRs can generally be identified using the NCBI IgBLAST algorithm. Those of skill in the art will recognize that different sequence algorithms can provide slightly different descriptions of the location of the CDRs in a particular antibody amino acid sequence. In some cases, the heavy chain CDRs occur at amino acid positions 31-35 (CDR1), 50-65 (CDR2) and 96-102 (CDR3). In some cases, the light chain CDRs occur at amino acid positions 24-34 (CDR1), 50-56 (CDR2) and 89-97 (CDR3). In some embodiments, the CDRs are represented as depicted in FIG. 1.

The ability of a particular antibody to recognize the same epitope as another antibody is typically determined by the ability of one antibody to competitively inhibit binding of the second antibody to the antigen, e.g., to CXCR7 or a fragment or fusion thereof. Any of a number of competitive binding assays can be used to measure competition between two antibodies to the same antigen. An exemplary assay is a Biacore assay. Briefly in these assays, binding sites can be mapped in structural terms by testing the ability of interactants, e.g. different antibodies, to inhibit the binding of another. Injecting two consecutive antibody samples in sufficient concentration can identify pairs of competing antibodies for the same binding epitope. The antibody samples should have the potential to reach a significant saturation with each injection. The net binding of the second antibody injection is indicative for binding epitope analysis. Two response levels can be used to describe the boundaries of perfect competition versus non-competing binding due to distinct epitopes. The relative amount of binding response of the second antibody injection relative to the binding of identical and distinct binding epitopes determines the degree of epitope overlap. Antibodies may recognize linear or conformational epitopes, hence antibodies may be competitive while recognizing dissimilar and distal epitopes.

Other conventional immunoassays known in the art can be used in the present invention. For example, antibodies can be differentiated by the epitope to which they bind using a sandwich ELISA assay. This is carried out by using a capture antibody to coat the surface of a well. A subsaturating concentration of tagged-antigen is then added to the capture surface. This protein will be bound to the antibody through a specific antibody:epitope interaction. After washing a second antibody, which has been covalently linked to a detectable moiety (e.g., HRP, with the labeled antibody being defined as the detection antibody) is added to the ELISA. If this antibody recognizes the same epitope as the capture antibody it will be unable to bind to the target protein as that particular epitope will no longer be available for binding. If however this second antibody recognizes a different epitope on the target protein it will be able to bind and this binding can be detected by quantifying the level of activity (and hence antibody bound) using a relevant substrate. The background is defined by using a single antibody as both capture and detection antibody, whereas the maximal signal can be established by capturing with an antigen specific antibody and detecting with an antibody to the tag on the antigen. By using the background and maximal signals as references, antibodies can be assessed in a pair-wise manner to determine epitope specificity.

A first antibody is considered to competitively inhibit binding of a second antibody, if binding of the second antibody to the antigen is reduced by at least 30%, usually at least about 40%, 50%, 60% or 75%, and often by at least about 90%, in the presence of the first antibody using any of the assays described above.

Methods of preparing polyclonal antibodies are known to the skilled artisan. Polyclonal antibodies can be raised in a mammal, e.g., by one or more injections of an immunizing agent and, if desired, an adjuvant. Typically, the immunizing agent and/or adjuvant will be injected in the mammal by multiple subcutaneous or intraperitoneal injections. The immunizing agent may include a protein encoded by a nucleic acid or fragment thereof or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

The antibodies may, alternatively, be monoclonal antibodies. Monoclonal antibodies may be prepared using hybridoma methods, such as those described by Kohler & Milstein, *Nature* 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro. The immunizing agent will typically include a CXCR7 polypeptide, or a fragment or fusion thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, pp. 59-103 (1986)). Immortalized cell lines are usually transformed mammalian cells, particularly myeloma cells of rodent, bovine and human origin. Usually, rat or mouse myeloma cell lines are employed. The hybridoma cells can be cultured in a suitable culture medium that contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

In some embodiments the antibodies of the invention are chimeric or humanized antibodies that compete with antibodies comprising SEQ ID NO:23 and SEQ ID NO:25, or SEQ ID NO:27 and SEQ ID NO:29 for binding to CXCR7. As noted above, humanized forms of antibodies are chimeric immunoglobulins in which residues from a complementary determining region (CDR) of human antibody are replaced by residues from a CDR of a non-human species such as mouse, rat or rabbit having the desired specificity, affinity and capacity. For example, the CDRs of SEQ ID NO:23 and SEQ ID NO:25, or SEQ ID NO:27 and SEQ ID NO:29, can be inserted into the framework of a human antibody.

Human antibodies can be produced using various techniques known in the art, including phage display libraries (Hoogenboom & Winter, *J. Mol. Biol.* 227:381 (1991); Marks et al., *J. Mol. Biol.* 222:581 (1991)). The techniques of Cole et al. and Boerner et al. are also available for the preparation of human monoclonal antibodies (Cole et al., *Monoclonal Antibodies and Cancer Therapy*, p. 77 (1985) and Boerner et al., *J. Immunol.* 147(1):86-95 (1991)). Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, e.g., in U.S. Pat. Nos. 5,545,807; 5,545,806; 5,569,825; 5,625,126; 5,633,425; 5,661,016, and in the following scientific publications: Marks et al., *Bio/Technology* 10:779-783 (1992); Lonberg et al., *Nature* 368:856-859 (1994); Morrison, *Nature* 368:812-13 (1994); Fishwild et al., Nature Biotechnology 14:845-51 (1996); Neuberger, *Nature Biotechnology* 14:826 (1996); Lonberg & Huszar, *Intern. Rev. Immunol.* 13:65-93 (1995).

In some embodiments, the antibodies of the invention are single chain Fvs (scFvs). The $V_H$ and the $V_L$ regions (e.g., SEQ ID NO:12 and SEQ ID NO:14, or SEQ ID NO:16 and SEQ ID NO: 18) of a scFv antibody comprise a single chain which is folded to create an antigen binding site similar to that found in two chain antibodies. Once folded, noncovalent interactions stabilize the single chain antibody. While the $V_H$ and $V_L$ regions of some antibody embodiments can be directly joined together, one of skill will appreciate that the regions may be separated by a peptide linker consisting of one or more amino acids. Peptide linkers and their use are well-known in the art. See, e.g., Huston et al., *Proc. Nat'l Acad. Sci. USA* 8:5879 (1988); Bird et al., *Science* 242:4236 (1988); Glockshuber et al., *Biochemistry* 29:1362 (1990); U.S. Pat. Nos. 4,946,778, 5,132,405 and Stemmer et al., *Biotechniques* 14:256-265 (1993). Generally the peptide linker will have no specific biological activity other than to join the regions or to preserve some minimum distance or other spatial relationship between the $V_H$ and $V_L$. However, the constituent amino acids of the peptide linker may be selected to influence some property of the molecule such as the folding, net charge, or hydrophobicity. Single chain Fv (scFv) antibodies optionally include a peptide linker of no more than 50 amino acids, generally no more than 40 amino acids, preferably no more than 30 amino acids, and more preferably no more than 20 amino acids in length. In some embodiments, the peptide linker is a concatamer of the sequence Gly-Gly-Gly-Gly-Ser (SEQ ID NO:41), preferably 2, 3, 4, 5, or 6 such sequences. However, it is to be appreciated that some amino acid substitutions within the linker can be made. For example, a valine can be substituted for a glycine.

Methods of making scFv antibodies have been described. See, Huse et al., *Science* 246:1275-1281 (1989); Ward et al., *Nature* 341:544-546 (1989); and Vaughan et al., *Nature Biotech.* 14:309-314 (1996). In brief, mRNA from B-cells from an immunized animal is isolated and cDNA is prepared. The cDNA is amplified using primers specific for the variable regions of heavy and light chains of immunoglobulins. The PCR products are purified and the nucleic acid sequences are joined. If a linker peptide is desired, nucleic acid sequences that encode the peptide are inserted between the heavy and light chain nucleic acid sequences. The nucleic acid which encodes the scFv is inserted into a vector and expressed in the appropriate host cell. The scFv that specifically bind to the desired antigen are typically found by panning of a phage display library. Panning can be performed by any of several methods. Panning can conveniently be performed using cells expressing the desired antigen on their surface or using a solid surface coated with the desired antigen. Conveniently, the surface can be a magnetic bead. The unbound phage are washed off the solid surface and the bound phage are eluted.

Finding the antibody with the highest affinity is dictated by the efficiency of the selection process and depends on the number of clones that can be screened and the stringency with which it is done. Typically, higher stringency corresponds to more selective panning. If the conditions are too stringent, however, the phage will not bind. After one round of panning, the phage that bind to CXCR7 coated plates or to cells expressing CXCR7 on their surface are expanded in *E. coli* and subjected to another round of panning. In this way, an enrichment of many fold occurs in 3 rounds of panning. Thus, even when enrichment in each round is low, multiple rounds of panning will lead to the isolation of rare phage and the genetic material contained within which encodes the scFv with the highest affinity or one which is better expressed on phage.

Regardless of the method of panning chosen, the physical link between genotype and phenotype provided by phage display makes it possible to test every member of a cDNA library for binding to antigen, even with large libraries of clones.

In one embodiment, the antibodies are bispecific antibodies. Bispecific antibodies are monoclonal, including, but not limited to, human or humanized, antibodies that have binding specificities for at least two different antigens or that have binding specificities for two epitopes on the same antigen. In one embodiment, one of the binding specificities is for a CXCR7 protein, the other one is for another different cancer antigen. Alternatively, tetramer-type technology may create multivalent reagents.

In some embodiments, the antibody is conjugated to an effector moiety. The effector moiety can be any number of molecules, including detectable labeling moieties such as radioactive labels or fluorescent labels, or can be a therapeutic moiety.

In other embodiments, the therapeutic moiety is a cytotoxic agent. In this method, targeting the cytotoxic agent to cancer tissue or cells, results in a reduction in the number of afflicted cells, thereby reducing symptoms associated with the cancer. Cytotoxic agents are numerous and varied and include, but are not limited to, cytotoxic drugs or toxins or active fragments of such toxins. Suitable toxins and their corresponding fragments include diphtheria A chain, exotoxin A chain, ricin A chain, abrin A chain, curcin, crotin, phenomycin, enomycin, auristatin and the like. Cytotoxic agents also include radiochemicals made by conjugating radioisotopes to antibodies of the invention.

III. Immunoassays

The antibodies of the invention can be used to detect CXCR7 or CXCR7-expressing cells using any of a number of well recognized immunological binding assays (see, e.g., U.S. Pat. Nos. 4,366,241; 4,376,110; 4,517,288; and 4,837,168). For a review of the general immunoassays, see also Methods in Cell Biology, Vol. 37, Asai, ed. Academic Press, Inc. New York (1993); *Basic and Clinical Immunology* 7th Edition, Stites & Terr, eds. (1991).

Thus, the present invention provides methods of detecting cells that express CXCR7. In one method, a biopsy is performed on the subject and the collected tissue is tested in vitro. The tissue or cells from the tissue is then contacted, with an anti-CXCR7 antibody of the invention. Any immune complexes which result indicate the presence of a CXCR7 protein in the biopsied sample. To facilitate such detection, the antibody can be radiolabeled or coupled to an effector molecule which is a detectable label, such as a fluorescent label. In another method, the cells can be detected in vivo using imaging systems. Then, the localization of the label is determined. A conventional method for visualizing diagnostic imaging can be used. For example, paramagnetic isotopes can be used for MRI. Internalization of the antibody may be important to extend the life within the organism beyond that provided by extracellular binding, which will be susceptible to clearance by the extracellular enzymatic environment coupled with circulatory clearance.

CXCR7 proteins can also be detected using standard immunoassay methods and the antibodies of the invention. Standard methods include, for example, radioimmunoassay, sandwich immunoassays (including ELISA), immunofluorescence assays, Western blot, affinity chromatography (affinity ligand bound to a solid phase), and in situ detection with labeled antibodies. A secondary detection agent may also be employed, e.g., goat anti-mouse FITC. A general overview of the applicable technology can be found in Harlow & Lane, *Antibodies: A Laboratory Manual* (1988).

The present invention provides methods of detecting a cancer cell, including methods of providing a prognosis or diagnosis of cancer. CXCR7 is expressed in nearly every cancer cell tested to date, whereas normal (non-cancer) expression of CXCR7 appears to be limited to the kidney and some brain cells as well as in certain developmental stages of fetal liver. See, e.g., PCT/US04/34807 and U.S. patent application Ser. Nos. 10/698,541 and 10/912,638. Therefore, expression of CXCR7 in a cell, and in particular, in a non-fetal cell and/or a cell other than a kidney or brain cell, indicates the likely presence of a cancer cell. The presence of CXCR7 in the tissue cells or vascular endothelium of a tissue may also indicate the presence of a cancer. In some cases, samples containing CXCR7-expressing cells are confirmed for the presence of cancer cells using other methods known in the art.

According to yet another aspect of the invention, methods for selecting a course of treatment of a subject having or suspected of having cancer are provided. The methods include obtaining from the subject a biological sample, contacting the sample with antibodies or antigen-binding fragments thereof that bind specifically to CXCR7, detecting the presence or absence of antibody binding, and selecting a course of treatment appropriate to the cancer of the subject. In some embodiments, the treatment is administering CXCR7 antibodies of the invention to the subject.

The present invention provides for methods of diagnosing human diseases including, but not limited to cancer, e.g., carcinomas, gliomas, mesotheliomas, melanomas, lymphomas, leukemias, adenocarcinomas, breast cancer, ovarian cancer, cervical cancer, glioblastoma, leukemia, lymphoma, prostate cancer, and Burkitt's lymphoma, head and neck cancer, colon cancer, colorectal cancer, non-small cell lung cancer, small cell lung cancer, cancer of the esophagus, stomach cancer, pancreatic cancer, hepatobiliary cancer, cancer of the gallbladder, cancer of the small intestine, rectal cancer, kidney cancer, bladder cancer, prostate cancer, penile cancer, urethral cancer, testicular cancer, cervical cancer, vaginal cancer, uterine cancer, ovarian cancer, thyroid cancer, parathyroid cancer, adrenal cancer, pancreatic endocrine cancer, carcinoid cancer, bone cancer, skin cancer, retinoblastomas, Hodgkin's lymphoma, non-Hodgkin's lymphoma (see, CANCER: PRINCIPLES AND PRACTICE (DeVita, V. T. et al. eds 1997) for additional cancers); as well as brain and neuronal dysfunction, such as Alzheimer's disease and multiple sclerosis; kidney dysfunction; rheumatoid arthritis; cardiac allograft rejection; atherosclerosis; asthma; glomerulonephritis; contact dermatitis; inflammatory bowel disease; colitis; psoriasis; reperfusion injury; as well as other disorders and diseases described herein.

IV. Modulators of CXCR7

A. Methods of Identifying Modulators of Chemokine Receptors

A number of different screening protocols can be utilized to identify agents that modulate the level of activity or function of CXCR7 in cells, particularly in mammalian cells, and especially in human cells. In general terms, the screening methods involve screening a plurality of agents to identify an agent that interacts with a polypeptide comprising any of SEQ ID NOS:2, 8, 9, 11, 12, 14, 15, 16, 17 or as otherwise described herein, including fragments of CXCR7 comprising these sequences, for example, by binding to a CXCR7 fragment and preventing antibodies of the invention from binding to the CXCR7 fragment or activating CXCR7. In some embodiments, an agent binds CXCR7 with at least about 1.5, 2, 3, 4, 5, 10, 20, 50, 100, 300, 500, or 1000 times the affinity of the agent for another protein. In some embodiments, the fragment of CXCR7 comprising the epitopes described herein (and optionally comprising further non-CXCR7 amino acids at the N and/or C termini) is no more than, e.g., 300, 250, 200, 150, 100, 50, 40, 30, 20 or fewer amino acids. In some embodiments, the CXCR7 fragment is any fragment having less than all of the amino acids in the full length CXCR7 polypeptide.

1. Chemokine Receptor Binding Assays

In some embodiments, CXCR7 modulators are identified by screening for molecules that compete with antibody of the invention from binding to a CXCR7 polypeptide, or fragment thereof. Those of skill in the art will recognize that there are a number of ways to perform competition analyses. In some embodiments, samples with CXCR7 are pre-incubated with a labeled antibody of the invention (e.g., an antibody comprising at least the CDRs of SEQ ID NO:23, SEQ ID NO:25, SEQ ID NO:27 and/or SEQ ID NO:29) and then contacted with a potential competitor molecule. Alteration (e.g., a decrease) of the quantity of antibody bound to CXCR7 in the presence of a test compound indicates that the test compound is a potential CXCR7 modulator.

Preliminary screens can be conducted by screening for agents capable of binding to a CXCR7, as at least some of the agents so identified are likely chemokine receptor modulators. The binding assays usually involve contacting CXCR7 with one or more test agents and allowing sufficient time for the protein and test agents to form a binding complex. Any binding complexes formed can be detected using any of a number of established analytical techniques. Protein binding assays include, but are not limited to, immunohistochemical binding assays, flow cytometry, radioligand binding, europium labeled ligand binding, biotin labeled ligand binding or other assays which maintain the conformation of CXCR7. The chemokine receptor utilized in such assays can be naturally expressed, cloned or synthesized. Binding assays may be used to identify agonists or antagonists. For example, by contacting CXCR7 with a potential agonist and measuring for CXCR7 activity, it is possible to identify those molecules that stimulate CXCR7 activity.

2. Cells and Reagents

The screening methods of the invention can be performed as in vitro or cell-based assays. In vitro assays are performed for example, using membrane fractions or whole cells comprising CXCR7. Cell based assays can be performed in any cells in which CXCR7 is expressed.

Cell-based assays involve whole cells or cell fractions containing CXCR7 to screen for agent binding or modulation of activity of CXCR7 by the agent. Exemplary cell types that can be used according to the methods of the invention include, e.g., any mammalian cells including leukocytes such as neutrophils, monocytes, macrophages, eosinophils, basophils, mast cells, and lymphocytes, such as T cells and B cells, leukemias, Burkitt's lymphomas, tumor cells, endothelial cells, pericytes, fibroblasts, cardiac cells, muscle cells, breast tumor cells, ovarian cancer carcinomas, cervical carcinomas, glioblastomas, liver cells, kidney cells, and neuronal cells, as well as fungal cells, including yeast. Cells can be primary cells or tumor cells or other types of immortal cell lines. Of course, CXCR7 can be expressed in cells that do not express an endogenous version of CXCR7, or in which expression has been induced.

In some cases, fragments of CXCR7, as well as protein fusions, can be used for screening. When molecules that compete for binding with CXCR7 ligands are desired, the CXCR7 fragments used are fragments capable of binding the antibodies of the invention. Alternatively, any fragment of CXCR7 can be used as a target to identify molecules that bind CXCR7. CXCR7 fragments can include any fragment of; e.g., at least 20, 30, 40, 50 amino acids up to a protein containing all but one amino acid of CXCR7. Typically, ligand-binding fragments will comprise transmembrane regions and/or most or all of the extracellular domains of CXCR7.

3. Signaling or Adhesion Activity

In some embodiments, signaling triggered by CXCR7 activation is used to identify CXCR7 modulators. Signaling activity of chemokine receptors can be determined in many ways. For example, signaling refers to a change in cell function or structure that results from the binding of the receptor to a naturally occurring ligand, (e.g., CXCR7 binding of SDF-1 or I-TAC) and can include receptor internalization, receptor-mediated signaling (e.g., activation of a mammalian G protein, induction of rapid and transient increase in the concentration of cytosolic free calcium), a cellular response function (e.g., stimulation of chemotaxis or release of inflammatory mediators), and the like. Alternatively signaling can be determined by detecting chemokine receptor-mediated cell adhesion. Interactions between chemokines and chemokine receptors can lead to rapid adhesion through the modification of integrin affinity and avidity. See, e.g., Laudanna, *Immunological Reviews* 186:37-46 (2002).

Signaling can also be measured by determining, qualitatively and quantitatively, secondary messengers, such as cyclic AMP or inositol phosphates, as well as phosphorylation or dephosphorylation events can also be monitored. See, e.g., Premack, et al. *Nature Medicine* 2: 1174-1178 (1996) and Bokoch, *Blood* 86:1649-1660 (1995).

In addition, other events downstream of CXCR7 activation can also be monitored to determine signaling activity. Downstream events include those activities or manifestations that occur as a result of stimulation of a chemokine receptor. Exemplary downstream events include, e.g., changed state of a cell (e.g., from normal to cancer cell or from cancer cell to non-cancerous cell). Cell responses include adhesion of cells (e.g., to endothelial cells). Established signaling cascades involved in angiogenesis (e.g., VEGF-mediated signaling) can also be monitored for effects caused by CXCR7 modulators. The ability of agents to promote angiogenesis can be evaluated, for example, in chick chorioallantoic membrane, as discussed by Leung et al. (1989) *Science* 246:1306-1309. Another option is to conduct assays with rat corneas, as discussed by Rastinejad et al. (1989) *Cell* 56:345-355. Other assays are disclosed in U.S. Pat. No. 5,840,693. Ovarian angiogenesis models can also be used (see, e.g., Zimmerman, R. C., et al. (2003) *J. Clin. Invest.* 112:659-669; Zimmerman, R. C., et al. (2001) *Microvasc. Res.* 62:15-25; and Hixenbaugh, E. A., et al. (1993) *Anat. Rec.* 235: 487-500).

Other screening methods are based on the observation that expression of certain regulatory proteins is induced by the presence or activation of CXCR7. Detection of such proteins can thus be used to indirectly determine the activity of CXCR7. A series of ELISA investigations were conducted to compare the relative concentration of various secreted proteins in the cell culture media for cells transfected with CXCR7 and untransfected cells. Through these studies it was determined that CXCR7 induces the production of a number of diverse regulatory proteins, including growth factors, chemokines, metalloproteinases and inhibitors of metalloproteinases. Thus, some of the screening methods that are provided involve determining whether a test agent modulates the production of certain growth factors, chemokines, metalloproteinases and inhibitors of metalloproteinases by CXCR7. In some instances, the assays are conducted with cells (or extracts thereof) that have been grown under limiting serum conditions as this was found to increase the production of the CXCR7-induced proteins.

The following proteins are examples of the various classes of proteins that were detected, as well as specific proteins within each class: (1) growth factors (e.g., GM-CSF); (2) chemokines (e.g., RANTES, MCP-1); (3) cytokines (eg IL-6) (4) metalloproteinase (e.g., MMP3); and (5) inhibitor of metalloproteinase (e.g., TIMP-1). It is expected that other proteins in these various classes can also be detected.

These particular proteins can be detected using standard immunological detection methods that are known in the art. One approach that is suitable for use in a high-throughput format, for example, are ELISAs that are conducted in multi-well plates. An ELISA kit for detecting TIMP-1 is available from DakoCytomation (Product Code No. EL513). ELISA kits for IL-6 and MMP3 can be obtained from R and D Systems. Further examples of suppliers of antibodies that specifically bind the proteins listed above are provided in the examples below. Proteins such as the metalloproteinases that are enzymes can also be detected by known enzymatic assays.

In other embodiments, potential modulators of CCX-CK2 are tested for their ability to modulate cell adhesion. Tumor cell adhesion to endothelial cell monolayers has been studied as a model of metastatic invasion (see, e.g., Blood and Zetter, *Biovhem. Biophys. Acta,* 1032, 89-119 (1990). These monolayers of endothelial cells mimic the lymphatic vasculature and can be stimulated with various cytokines and growth factors (e.g., TNFalpha and IL-1beta). Cells expressing CXCR7 can be evaluated for the ability to adhere to this monolayer in both static adhesion assays as well as assays where cells are under flow conditions to mimic the force of the vasculature in vivo. Additionally, assays to evaluate adhesion can also be performed in vivo (see, e.g., von Andrian, U. H. *Microcirculation.* 3(3):287-300 (1996)).

4. Validation

Agents that are initially identified by any of the foregoing screening methods can be further tested to validate the apparent activity. Preferably such studies are conducted with suitable animal models. The basic format of such methods involves administering a lead compound identified during an initial screen to an animal that serves as a disease model for humans and then determining if the disease (e.g., cancer, myocardial infarction, wound healing, or other diseases related to angiogenesis) is in fact modulated and/or the disease or condition is ameliorated. The animal models utilized in validation studies generally are mammals of any kind. Specific examples of suitable animals include, but are not limited to, primates, mice, rats and zebrafish.

In some embodiments, arthritis animal models are used to screen and/or validate therapeutic uses for agents that modulate CXCR7. Exemplary arthritis animal models include, e.g., the collagen-induced arthritis (CIA) animal model.

B. Agents that Interact with CXCR7

Modulators of CXCR7 (e.g., antagonists or agonists) can include, e.g., antibodies (including monoclonal, humanized or other types of binding proteins that are known in the art), small organic molecules, siRNAs, CXCR7 polypeptides or variants thereof, chemokines (including but not limited to SDF-1 and/or I-TAC), chemokine mimetics, chemokine polypeptides, etc.

The agents tested as modulators of CXCR7 can be any small chemical compound, or a biological entity, such as a polypeptide, sugar, nucleic acid or lipid. Alternatively, modulators can be genetically altered versions, or peptidomimetic versions, of a chemokine or other ligand. Typically, test compounds will be small chemical molecules and peptides. Essentially any chemical compound can be used as a potential modulator or ligand in the assays of the invention, although most often compounds that can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland) and the like.

In some embodiments, the agents have a molecular weight of less than 1,500 daltons, and in some cases less than 1,000, 800, 600, 500, or 400 or 300 daltons. The relatively small size of the agents can be desirable because smaller molecules have a higher likelihood of having physiochemical properties compatible with good pharmacokinetic characteristics, including oral absorption than agents with higher molecular weight. For example, agents less likely to be successful as drugs based on permeability and solubility were described by Lipinski et al. as follows: having more than 5 H-bond donors (expressed as the sum of OHs and NHs); having a molecular weight over 500; having a LogP over 5 (or MLogP over 4.15); and/or having more than 10 H-bond acceptors (expressed as the sum of Ns and Os). See, e.g., Lipinski et al. *Adv Drug Delivery Res* 23:3-25 (1997). Compound classes that are substrates for biological transporters are typically exceptions to the rule.

In one embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks." For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309-314 (1996) and PCT/US96/10287), carbohydrate libraries (see, e.g., Liang et al., *Science*, 274:1520-1522 (1996) and U.S. Pat. No. 5,593,853), small organic molecule libraries (see, e.g., benzodiazepines, Baum C&EN, Jan 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.).

V. Cancer, Angiogenesis and Other Biological Aspects of CXCR7

The antibodies of the invention can be contacted to a cell expressing CXCR7 in vitro, in vivo, or ex vivo (i.e., removed from a body, treated and returned to the body). The antibodies of the invention can be administered directly to the mammalian subject for modulation of chemokine receptor activity in vivo. In some embodiments, the antibodies compete with SDFI and/or I-TAC for binding to CXCR7. In some embodiments, the antibodies do not comprise SEQ ID NO:23 and/or SEQ ID NO:25, or SEQ ID NO:27 and/or SEQ ID NO:29.

In some embodiments, the CXCR7 antibodies are administered to a subject having cancer. In some cases, CXCR7 modulators are administered to treat cancer, e.g., carcinomas, gliomas, mesotheliomas, melanomas, lymphomas, leukemias, adenocarcinomas, breast cancer, ovarian cancer, cervical cancer, glioblastoma, leukemia, lymphoma, prostate cancer, and Burkitt's lymphoma, head and neck cancer, colon cancer, colorectal cancer, non-small cell lung cancer, small cell lung cancer, cancer of the esophagus, stomach cancer, pancreatic cancer, hepatobiliary cancer, cancer of the gallbladder, cancer of the small intestine, rectal cancer, kidney cancer, bladder cancer, prostate cancer, penile cancer, urethral cancer, testicular cancer, cervical cancer, vaginal cancer, uterine cancer, ovarian cancer, thyroid cancer, parathyroid cancer, adrenal cancer, pancreatic endocrine cancer, carcinoid cancer, bone cancer, skin cancer, retinoblastomas, Hodgkin's lymphoma, non-Hodgkin's lymphoma (see, CANCER: PRINCIPLES AND PRACTICE (DeVita, V. T. et al. eds 1997) for additional cancers); as well as brain and neuronal dysfunction, such as Alzheimer's disease and multiple sclerosis; kidney dysfunction; rheumatoid arthritis; cardiac allograft rejection; atherosclerosis; asthma; glomerulonephritis; contact dermatitis; inflammatory bowel disease; colitis; psoriasis; reperfusion injury; as well as other disorders and diseases described herein.

The present invention also encompasses decreasing angiogenesis in any subject in need thereof by administering antibodies of the invention. For example, decreasing CXCR7 activity by contacting CXCR7 with an antibody of the invention, thereby decreasing angiogenesis, is useful to inhibit formation, growth and/or metastasis of tumors, especially solid tumors. Description of embodiments relating to modulated CXCR7 and angiogenesis are described in, e.g., U.S. patent application Ser. No. 11/050,345.

Other disorders involving unwanted or problematic angiogenesis include rheumatoid arthritis; psoriasis; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; disease of excessive or abnormal stimulation of endothelial cells, including intestinal adhesions, Crohn's disease, skin diseases such as psoriasis, excema, and scleroderma, diabetes, diabetic retinopathy, retinopathy of prematurity, age-related macular degeneration, atherosclerosis, scleroderma, wound granulation and hypertrophic scars, i.e., keloids, and diseases that have angiogenesis as a pathologic consequence such as cat scratch disease and ulcers (*Helicobacter pylori*), can also be treated with antibodies of the invention. Angiogenic inhibitors can be used to prevent or inhibit adhesions, especially intra-peritoneal or pelvic adhesions such as those resulting after open or laproscopic surgery, and bum contractions. Other conditions which should be beneficially treated using the angiogenesis inhibitors include prevention of scarring following transplantation, cirrhosis of the liver, pulmonary fibrosis following acute respiratory distress syndrome or other pulmonary fibrosis of the newborn, implantation of temporary prosthetics, and adhesions after surgery between the brain and the dura. Endometriosis, polyposis, cardiac hypertrophyy, as well as obesity, may also be treated by inhibition of angiogenesis. These disorders may involve increases in size or growth of other types of normal tissue, such as uterine fibroids, prostatic hypertrophy, and amyloidosis. Antibodies of the present invention may be used prophylactically or therapeutically for any of the disorders or diseases described herein.

Decreasing CXCR7 activity with the antibodies of the present invention can also be used in the prevention of neovascularization to effectively treat a host of disorders. Thus, for example, the decreasing angiogenesis can be used as part of a treatment for disorders of blood vessels (e.g., hemangiomas and capillary proliferation within atherosclerotic plaques), muscle diseases (e.g., myocardial angiogenesis, myocardial infarction or angiogenesis within smooth muscles), joints (e.g., arthritis, hemophiliac joints, etc.), and other disorders associated with angiogenesis. Promotion of angiogenesis can also aid in accelerating various physiological processes and treatment of diseases requiring increased vascularization such as the healing of wounds, fractures, and burns, inflammatory diseases, ischeric heart, and peripheral vascular diseases.

The antibodies of the present invention may also be used to enhance wound healing. Without intending to limit the invention to a particular mechanism of action, it may be that antagonism of CXCR7 allows for endogenous ligands to instead bind to lower affinity receptors, thereby triggering enhanced wound healing. For example, SDF-1 binds to both CXCR7 and CXCR4, but binds to CXCR4 with a lower affinity. Similarly, I-TAC binds to CXCR3 with a lower affinity than I-TAC binds to CXCR7. By preventing binding of these ligands to CXCR7, CXCR7 antagonists may allow the ligands to bind to the other receptors, thereby enhancing wound healing. Thus, the antagonism of CXCR7 to enhance wound healing may be mediated by a different mechanism than enhancing wound healing by stimulating CXCR7 activity with an agonist.

Aside from treating disorders and symptoms associated with neovascularization, the inhibition of angiogenesis can be used to modulate or prevent the occurrence of normal physiological conditions associated with neovascularization. Thus, for example the inventive method can be used as a birth control. In accordance with the present invention, decreasing CXCR7 activity within the ovaries or endometrium can attenuate neovascularization associated with ovulation, implantation of an embryo, placenta formation, etc.

Inhibitors of angiogenesis have yet other therapeutic uses. For example, the antibodies of the present invention may be used for the following:

(a) Adipose tissue ablation and treatment of obesity. See, e.g, Kolonin et al., *Nature Medicine* 10(6):625-632 (2004);

(b) Treatment of preclampsia. See, e.g., Levine et al., *N. Engl. J. Med.* 350(7): 672-683 (2004); Maynard, et al., *J. Clin. Invest.* 111(5): 649-658 (2003); and (c) Treatment of cardiovascular disease. See, e.g., March, et al., *Am. J. Physiol. Heart Circ. Physiol.* 287:H458-H463 (2004); Rehman et al., *Circulation* 109: 1292-1298 (2004).

VI. Administration and Pharmaceutical Compositions

The pharmaceutical compositions of the invention may comprise, e.g., an antibody of the present invention and a pharmaceutically acceptable carrier. Pharmaceutically acceptable carriers are determined in part by the particular composition being administered, as well as by the particular method used to administer the composition. Accordingly, there is a wide variety of suitable formulations of pharmaceutical compositions of the present invention (see, e.g., *Remington's Pharmaceutical Sciences,* 17$^{th}$ ed. 1985)).

Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. In the practice of this invention, compositions can be administered, for example, orally, nasally, topically, intravenously, intraperitoneally, subcutaneously, or intrathecally. The formulations of compounds can be presented in unit-dose or multi-dose sealed containers, such as ampoules and vials. Solutions and suspensions can be prepared from sterile powders, granules, and tablets of the kind previously described.

The composition can be administered by means of an infusion pump, for example, of the type used for delivering insulin or chemotherapy to specific organs or tumors. Compositions of the inventions can be injected using a syringe or catheter directly into a tumor or at the site of a primary tumor prior to or after excision; or systemically following excision of the primary tumor. The compositions of the invention can be administered topically or locally as needed. For prolonged local administration, the antibodies may be administered in a controlled release implant injected at the site of a tumor. Alternatively an individual's cells can be transfected ex vivo with plasmids so as to express the antibody of the invention and subsequently injected at the site of the tumor. For topical treatment of a skin condition, the enzyme antibodies may be administered to the skin in an ointment or gel.

In some embodiments, CXCR7 antibodies of the present invention can be administered in combination with other appropriate therapeutic agents, including, e.g., chemotherapeutic agents, radiation, etc. Selection of the appropriate agents for use in combination therapy may be made by one of ordinary skill in the art, according to conventional pharmaceutical principles. The combination of therapeutic agents may act synergistically to effect the treatment or prevention of the various disorders such as, e.g., cancer, wounds, kidney dysfunction, brain dysfunction or neuronal dysfunction. Using this approach, one may be able to achieve therapeutic efficacy with lower dosages of each agent, thus reducing the potential for adverse side effects.

The dose administered to a patient, in the context of the present invention should be sufficient to effect a beneficial response in the subject over time (e.g., to reduce tumor size or tumor load). The optimal dose level for any patient will depend on a variety of factors including the efficacy of the specific modulator employed, the age, body weight, physical activity, and diet of the patient, on a possible combination with other drugs, and on the severity of a particular disease. The size of the dose also will be determined by the existence, nature, and extent of any adverse side-effects that accompany the administration of a particular compound or vector in a particular subject.

In determining the effective amount of the antibody to be administered a physician may evaluate circulating plasma levels of the antibody, antibody toxicity, and the production of anti-antibody antibodies. In general, the dose equivalent of an antibody is from about 1 ng/kg to 10 mg/kg for a typical subject.

For administration, the antibodies of the present invention can be administered at a rate determined by the LD-50 of the antibody, and the side-effects of the antibody at various concentrations, as applied to the mass and overall health of the subject. Clearance of the antibody by the recipient's immune system may also affect the suitable dosage to be administered. Administration can be accomplished via single or divided doses.

The compositions containing antibodies of the invention can be administered for therapeutic or prophylactic treatments. In therapeutic applications, compositions are administered to a patient suffering from a disease (e.g., a cancer, arthritis or other CXCR7-related disease or disorder) in an amount sufficient to cure or at least partially arrest the disease and its complications, e.g., decreased size of tumor, etc. An amount adequate to accomplish this is defined as a "therapeutically effective dose." Amounts effective for this use will depend upon the severity of the disease and the general state of the patient's health. Single or multiple administrations of the compositions may be administered depending on the dosage and frequency as required and tolerated by the patient. In any event, the composition should provide a sufficient quantity of the agents of this invention to effectively treat the patient. An amount of modulator that is capable of preventing or slowing the development of cancer in a mammal is referred to as a "prophylactically effective dose." The particular dose required for a prophylactic treatment will depend upon the medical condition and history of the mammal, the particular cancer being prevented, as well as other factors such as age, weight, gender, administration route, efficiency, etc. Such prophylactic treatments may be used, e.g., in a mammal who has previously had cancer to prevent a recurrence of the cancer, or in a mammal who is suspected of having a significant likelihood of developing cancer.

VII. Combination Therapies

Antibodies of the invention can be supplied alone or in conjunction with one or more other drugs. Possible combination partners can include, e.g., additional anti-angiogenic factors and/or chemotherapeutic agents (e.g., cytotoxic agents) or radiation, a cancer vaccine, an immunomodulatory agent, an anti-vascular agent, a signal transduction inhibitor, an antiproliferative agent, or an apoptosis inducer.

Antibodies of the invention can be used in conjunction with antibodies and peptides that block integrin engagement, proteins and small molecules that inhibit metalloproteinases (e.g., marmistat), agents that block phosphorylation cascades within endothelial cells (e.g., herbamycin), dominant negative receptors for known inducers of angiogenesis, antibodies against inducers of angiogenesis or other compounds that block their activity (e.g., suramin), or other compounds (e.g., retinoids, IL-4, interferons, etc.) acting by other means. Indeed, as such factors may modulate angiogenesis by different mechanisms, employing antibodies of the invention in combination with other antiangiogenic agents can potentiate a more potent (and potentially synergistic) inhibition of angiogenesis within the desired tissue.

Anti-angiogenesis agents, such as MMP-2 (matrix-metalloprotienase 2) inhibitors, MMP-9 (matrix-metalloprotienase 9) inhibitors, and COX-II (cyclooxygenase II) inhibitors, can be used in conjunction with antibodies of the invention and pharmaceutical compositions described herein. Anti-CXCR7 antibodies of the invention can also be used with signal transduction inhibitors, such as agents that can inhibit EGFR (epidermal growth factor receptor) responses, such as EGFR antibodies, EGF antibodies, and molecules that are EGFR inhibitors; VEGF (vascular endothelial growth factor) inhibitors, such as VEGF receptors and molecules that can inhibit VEGF; and erbB2 receptor inhibitors, such as organic molecules or antibodies that bind to the erbB2 receptor, for example, HERCEPTIN™ (Genentech, Inc. of South San Francisco, Calif., USA).

Anti-CXCR7 antibodies of the invention can also be combined with other drugs including drugs that promote angiogenesis and/or wound healing. Those of skill in the art will appreciate that one can incorporate one or more medicosurgically useful substances or therapeutic agents, e.g., those which can further intensify the angiogenic response, and/or accelerate and/or beneficially modify the healing process when the composition is applied to the desired site requiring angiogenesis. For example, to further promote angiogenesis, repair and/or tissue growth, at least one of several hormones, growth factors or mitogenic proteins can be included in the composition, e.g., fibroblast growth factor, platelet derived growth factor, macrophage derived growth factor, etc. In addition, antimicrobial agents can be included in the compositions, e.g., antibiotics such as gentamicin sulfate, or erythromycin. Other medico-surgically useful agents can include anti-inflammatories, analgesics, anesthetics, rubifacients, enzymes, antihistamines and dyes.

Anti-CXCR7 antibodies of the invention can also be combined with other drugs including drugs for treating arthritis. Examples of such agents include anti-inflammatory therapeutic agents. For example, glucocorticosteroids, such as prednisolone and methylprednisolone, are often-used anti-inflammatory drugs. Nonsteroidal anti-inflammatory drugs (NSAIDs) are also used to suppress inflammation. NSAIDs inhibit the cyclooxygenase (COX) enzymes, COX-1 and COX-2, which are central to the production of prostaglandins produced in excess at sites of inflammation. In addition, the inflammation-promoting cytokine, tumor necrosis factor α (TNFα), is associated with multiple inflammatory events, including arthritis, and anti-TNFα therapies are being used clinically.

VIII. Kits for Use in Diagnostic and/or Prognostic Applications

For use in diagnostic, research, and therapeutic applications suggested above, kits are also provided by the invention. In the diagnostic and research applications such kits may include any or all of the following: assay reagents, buffers, and the anti-CXCR7 antibodies of the invention. A therapeutic product may include sterile saline or another pharmaceutically acceptable emulsion and suspension base.

In addition, the kits may include instructional materials containing directions (i.e., protocols) for the practice of the methods of this invention. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLE

Production of antibodies to G-protein coupled receptors (GPCRs) has been notoriously difficult. We used the method of Genovac AG, DE outlined in Canadian Patent application CA 2 350 078. Antibodies that bind CXCR7 were created by inoculation of mice with cDNA expressing CXCR7 (SEQ ID NO:30). Briefly, CXCR7 was cloned into an expression vector and mice were inoculated with the vector by the gene gun method. At an appropriate time point, B cells were isolated, fused with myeloma cells by standard techniques, and fused hybridoma cells selected in in vitro culture. Supernatants from clonal cultures were analyzed for binding to cells stably transfected with CXCR7 by flow cytometry. Positive clones were amplified and subjected to further rounds of flow cytometric screening.

It was determined that monoclonal antibodies 6E10 and 11G8 bind to CXCR7. Antibodies 6E10 and 11G8 detected CXCR7 on transfectant cell lines that do not endogenously produce CXCR7, as well as on cells that endogenously express CXCR7, such as HeLa and MCF-7 (ATCC, VA). Additionally the antibodies were able to recognize the mouse homolog of CXCR7. For example, antibodies 6E10 and 11G8 detected CCX-CR2 on the mouse mammary tumor cell line 4T1 and Lewis lung carcinoma cells (ATCC, Va.). Antibodies 6E10 and 11G8, but not isotype controls were detected on an HEK 293 cell line transfected with CXCR7, but did not bind to HEK 293 cells transfected with an empty vector or those expressing other chemokine receptors (e.g., CXCR2).

The antibodies were also neutralizing, as demonstrated by radioligand competitive binding assays. Both antibodies 6E10 and 11G8 compete with both SDF-1 and I-TAC for binding to both mouse and human CXCR7. Antibody 11G8 typically exhibited a greater percentage inhibition of chemokine binding than did antibody 6E10.

Antibodies 6E10 and 11G8 also recognize CXCR7 in immunohistochemical (IHC) assays on fixed paraffin embedded tissue sections. In experiments on various tissue types, IHC staining with antibodies 6E10 and 11G8 matched the expression patterns determined with binding assays incorporating radiolabeled SDF or I-TAC on the respective tissues. For instance CXCR7 staining was found in sections of E13 fetal mouse, but not in sections of E17 fetal or adult mouse. CXCR7 staining was also seen in cytospins of cells stably expressing the human CXCR7.

The heavy and light chain variable region coding sequence, and predicted amino acid sequences were determined. 6E10's heavy chain variable region is contained in SEQ ID NO:23 (encoded by SEQ ID NO:22). 6E10's light chain variable region is contained in SEQ ID NO:25 (encoded by SEQ ID NO:24). 11G8's heavy chain variable region is contained in SEQ ID NO:27 (encoded by SEQ ID NO:26). 11G8's light chain variable region is contained in SEQ ID NO:29 (encoded by SEQ ID NO:28)

We have established that both 11G8 and 6E10 antibodies recognize CXCR7 receptor expressed on the surface of cells by FACS. This is represented as an increase in florescent signal (filled) over background (open line) along the X axis of FACS plot (FIG. 2). To interrogate which amino acid residues 11G8 and 6E10 recognize and bind to, a number of short peptides (0.5-5 µg) derived from the CXCR7 sequence were pre-incubated with either antibody (0.5-5 µg) in 100 µl PBS. This mixture was then incubated with 500,000 cells expressing CXCR7 for 15 minutes at room temperature. If the antibody recognized the sequence encoded by the peptide, then the peptide would effectively compete antibody away from binding to the cell associated receptor resulting in a subsequent reduction in florescence on a FACS plot. If the sequence did not interact with either antibody, then no reduction would be observed. These readouts are exemplified in FIG. 2 with "no peptide" representing incomplete antibody staining, "peptide 2.2.1" representing peptide competition, and "peptide 2.3.4" representing no peptide competition. Through slight alternations of the peptide sequence in this assay, the minimal peptide sequence necessary for antibody recognition was discerned. FIG. 3 illustrates a summary of peptides that competed with either antibody 11G8 or 6E10.

Although the invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

All publications, databases, Genbank sequences, patents, and patent applications cited in this specification are herein incorporated by reference as if each was specifically and individually indicated to be incorporated by reference.

What is claimed is:

1. A monoclonal antibody that binds to:
   a polypeptide consisting of FSDISWPC (SEQ ID NO:12); or
   a polypeptide consisting of SWPCNSSDCIVV (SEQ ID NO:15),
   wherein the antibody does not comprise the complementarity determining regions (CDRs) of the variable regions displayed in SEQ ID NO:23, SEQ ID NO:25, SEQ ID NO:27, or SEQ ID NO:29; and
   the antibody competes with SDF-1 and I-TAC for binding to CXCR7 and causes a shift of 0.5 logs or higher when competition of the antibody with SDF-1 or I-TAC is measured by FACS.

2. The antibody of claim 1, wherein the antibody is linked to a detectable label.

3. The antibody of claim 1, which is a humanized antibody.

4. The antibody of claim 1, wherein the antibody binds to the polypeptide consisting of FSDISWPC (SEQ ID NO:12).

5. The antibody of claim 1, wherein the antibody binds to the polypeptide consisting of SWPCNSSDCIVV (SEQ ID NO:15).

6. The antibody of claim 1, wherein the antibody competes with SDF-1 for binding to CXCR7.

7. A pharmaceutical composition comprising a pharmaceutically acceptable excipient and the antibody of claim 1.

8. The pharmaceutical composition of claim 7, wherein the antibody is a humanized antibody.

9. The pharmaceutical composition of claim 7, wherein the antibody binds to the polypeptide consisting of FSDISWPC (SEQ ID NO:12).

10. The pharmaceutical composition of claim 7, wherein the antibody binds to the polypeptide consisting of SWPCNSSDCIVV (SEQ ID NO:15).

11. The antibody of claim 1, wherein the antibody is linked to a cytotoxic agent.

12. A method of detecting a cell expressing CXCR7 in a biological sample, the method comprising contacting the biological sample with an antibody of claim 1 and detecting the presence of the antibody.

* * * * *